(12) United States Patent  
Kaminski et al.

(10) Patent No.: US 7,902,728 B2
(45) Date of Patent: Mar. 8, 2011

(54) THERMALLY ENHANCED PIEZOELECTRIC ELEMENT

(75) Inventors: Perry Kaminski, Stehekin, WA (US); Yu-Chi Chu, Brier, WA (US)

(73) Assignee: UST, Inc., Seattle, WA (US)

( * ) Notice: Subject to any disclaimer, the term of this patent is extended or adjusted under 35 U.S.C. 154(b) by 319 days.

(21) Appl. No.: 12/163,196

(22) Filed: Jun. 27, 2008

(65) Prior Publication Data

US 2008/0262358 A1    Oct. 23, 2008

Related U.S. Application Data

(63) Continuation of application No. 11/458,978, filed on Jul. 20, 2006, now Pat. No. 7,405,510.

(60) Provisional application No. 60/700,772, filed on Jul. 20, 2005.

(51) Int. Cl.
H01L 41/083 (2006.01)
(52) U.S. Cl. .......... 310/346; 310/322; 310/334; 310/366
(58) Field of Classification Search ................. 310/322, 310/328, 334, 366, 346
See application file for complete search history.

(56) References Cited

U.S. PATENT DOCUMENTS

| | | | |
|---|---|---|---|
| 4,499,566 A | | 2/1985 | Abbott |
| 4,752,712 A | * | 6/1988 | Tomita et al. ................. 310/328 |
| 4,876,776 A | | 10/1989 | Whatmore et al. |
| 5,168,189 A | * | 12/1992 | Dam et al. .................... 310/328 |
| 5,233,260 A | * | 8/1993 | Harada et al. ................. 310/328 |
| 5,625,149 A | | 4/1997 | Gururaja et al. |
| 5,686,777 A | * | 11/1997 | Chang ........................... 310/326 |
| 5,873,973 A | | 2/1999 | Koon et al. |
| 5,945,770 A | | 8/1999 | Hanafy |
| 6,608,428 B2 | | 8/2003 | Nishimura et al. |
| 6,822,374 B1 | * | 11/2004 | Smith et al. .................... 310/334 |
| 7,071,599 B2 | | 7/2006 | Namerikawa et al. |
| 7,378,779 B2 | | 5/2008 | Kaminski et al. |
| 7,405,510 B2 | * | 7/2008 | Kaminski et al. ............. 310/334 |
| 7,678,054 B2 | * | 3/2010 | Okazaki et al. ............... 600/459 |
| 2002/0182397 A1 | | 12/2002 | Whatley |
| 2003/0020372 A1 | * | 1/2003 | Baker et al. ................... 310/346 |
| 2003/0127947 A1 | * | 7/2003 | Chandran et al. ............. 310/328 |
| 2004/0032188 A1 | | 2/2004 | Bhardwaj |
| 2005/0179343 A1 | | 8/2005 | Johansson et al. |

FOREIGN PATENT DOCUMENTS

| DE | WO2004114425 A1 | 12/2004 |
|---|---|---|
| JP | 01293851 | 11/1989 |
| WO | WO2005078815 | 8/2005 |

OTHER PUBLICATIONS

U.S. Appl. No. 11/458,994, filed Jul. 20, 2006, Kaminski.
U.S. Appl. No. 11/458,978, filed Jul. 20, 2006, Kaminski.
U.S. Appl. No. 11/458,973, filed Jul. 20, 2006, Kaminski.

* cited by examiner

*Primary Examiner* — Thomas M Dougherty
(74) *Attorney, Agent, or Firm* — Brian G Forrest; Hughes Law Firm, PLLC

(57) ABSTRACT

A system and method for removing unwanted heat generated by a piezoelectric element of an ultrasound transducer. Some implementations have high thermal conductivity (HTC) material placed adjacent to the piezoelectric element. The HTC material can be thermally coupled to one or more heat sinks. Use of HTC material in conjunction with these piezoelectric element surfaces is managed to avoid degradation of propagating acoustic energy. Use of the HTC material in conjunction with heat sinks allows for creation of thermal paths away from the piezoelectric element. Active cooling of the heat sinks with water or air can further draw heat from the piezoelectric element. Further implementations form a composite matrix of thermally conductive material or interleave thermally conductive layers with piezoelectric material.

9 Claims, 17 Drawing Sheets

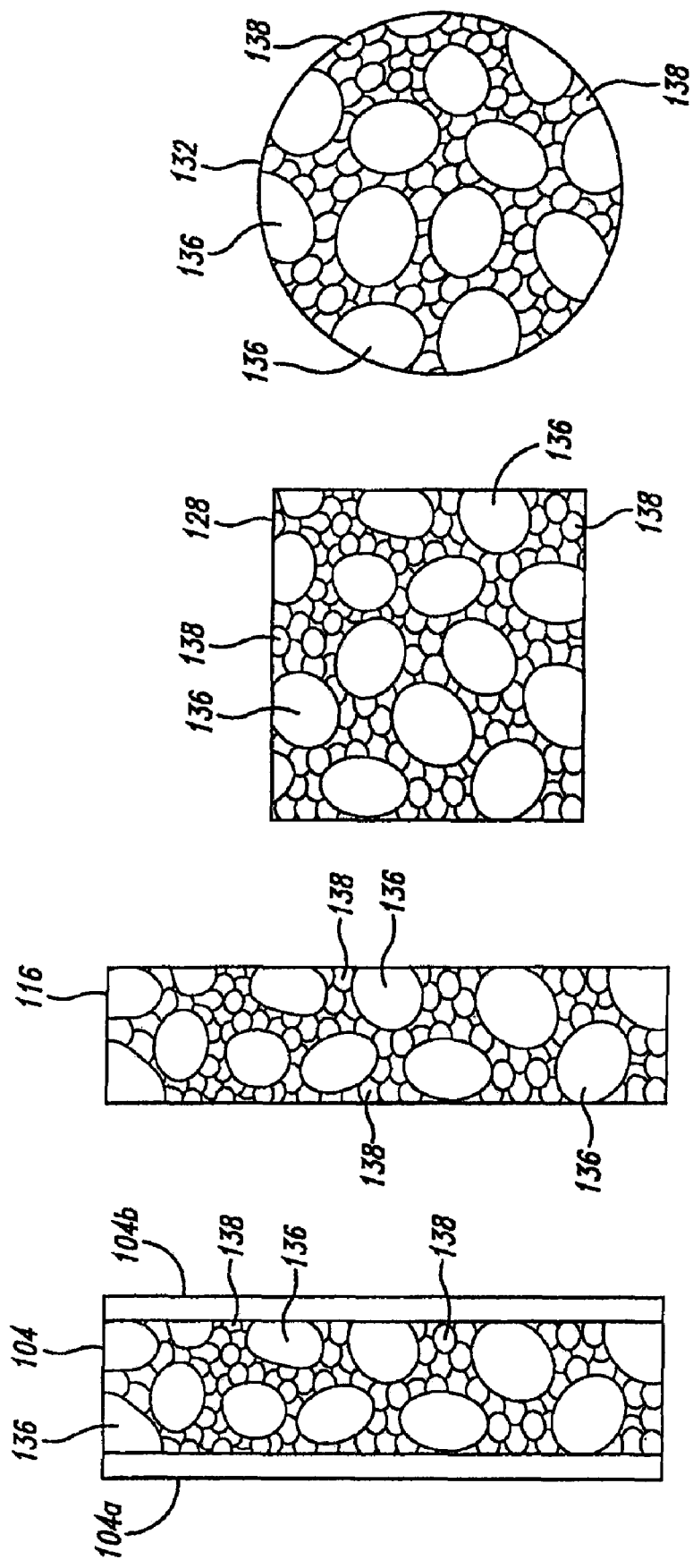

THERMALLY ENHANCED PIEZOELECTRIC ELEMENT

CROSS REFERENCE TO RELATED APPLICATIONS

This application is a continuation application of U.S. Ser. No. 11/458,978 filed Jul. 20, 2006, which claims priority benefit of provisional application Ser. No. 60/700,772 filed Jul. 20, 2005.

BACKGROUND OF THE INVENTION

1. Field of the Invention

The present invention is directed to ultrasound transducers for medical applications.

2. Description of the Related Art

Conventional ultrasound transducers used for medical applications, such as High Intensity Focused Ultrasound (HIFU), generate unwanted heat that can affect performance of the transducer. This unwanted heat is due to piezoelectric elements, used therein, having some inefficiency in converting electrical power into acoustic waves. Ceramic piezoelectric elements typically have low thermal conductivity (such as approximately one to two W/mC), which contributes in part to the unwanted heat producing undesirable elevated temperatures.

Some medical and other applications require transducer temperatures to be kept in narrow ranges. For example, when transducers are near or touching biological tissue not intended for treatment, the dosage for this untreated tissue must be held below an equivalent thermal dose of 43 degrees centigrade for 60 minutes. For temperatures above 43 degrees centigrade, equivalent thermal dose is proportional to approximately $2^{**}(T-43)$, where T is temperature in degrees centigrade. For example, an equivalent thermal dose will also occur at 44 degrees centigrade for approximately 30 minutes and at 50 degrees centigrade for approximately 30 seconds. If a transducer does not come into contact with a patient, generally higher temperatures are permitted, however, temperature levels in excess of 80 or 90 degrees centigrade are most likely to result in damage to the transducer and/or portions of electrical and/or mechanical elements supporting or otherwise associated with the transducer.

For instance, HIFU treatments can involve tens or hundreds of Watts of focused acoustic power resulting in acoustic intensities from 1,000 to 40,000 watts per square centimeter (although typical values are on the order of 2,000 W/cm$^2$); these values can be compared with a few milliwatts per square centimeter for typical diagnostic ultrasound applications. The HIFU treatments can include sound frequencies from one hundred kilohertz to over ten megahertz, with the most common range of 1-10 MHZ.

Conventional attempts at improving performance and lessening other unwanted effects include improving performance so less heat is generated, compensation through electronic controls and/or attempts at removing generated heat. Unfortunately, conventional approaches can lack effectiveness, be cumbersome and/or degrade performance.

A conventional first ultrasound transducer 10, as schematically depicted in FIG. 1 as having elements positioned along an illustrative X-dimension (with a depicted illustrative Y-dimension normal to the X-dimension) to include a rear medium 12, such as air, adjacent to a first piezoelectric element 14, such as a ceramic material, adjacent to a front layer 16. Air is generally useful for the rear medium since it acts as a near perfect reflector in cases where the acoustic impedance of the piezoelectric element 14 is much different than that of air (approximately 0.0004 MRayls). In operation, the front layer 16 is placed adjacent to a front medium 18, such as a tissue of a recipient of ultrasound 20.

The piezoelectric element 14 converts electrical energy into the ultrasound 20, which conducts through the front layer 16 into the front medium 18. The front layer 16 is typically fashioned to help match the acoustical impedance between the piezoelectric element 14 and the front medium 18 for better transfer of the ultrasound 20 from the piezoelectric element to the front medium. For impedance matching, the front layer 16 can be typically as thick as approximately one or more multiples (in particular implementations, odd multiples) of a quarter wavelength of an ultrasound frequency used in operation such as a center operational frequency. The front layer 16 would also have an acoustic impedance to help match impedances of the piezoelectric element 14 (having an acoustic impedance such as approximately 30-35 MRayls) and the front medium 18 (for instance, tissue has an acoustic impedance approximately 1.6 MRayls). The acoustic impedance of single matching layers, such as the front layer 16, can be typically chosen to be within the range of 4 to 8 MRayls. The thermal conductivity of a matching layer in a conventional transducer is often in the range of 1 to 3 W/mC, which is typically the result of loading an epoxy matrix with a higher acoustic impedance and lower acoustic attenuation material such as silicon dioxide or aluminum oxide powder.

Generally, an acoustic impedance for the front layer 16 somewhere between that of the piezoelectric element 14 and that of the front medium 18 is used for acoustic impedance matching of the piezoelectric element and the front medium. Unfortunately, materials used for acoustic impedance matching tend to give conventional matching layers such as the front layer 16 low thermal conductivity. For the front layer 16 between the piezoelectric element 14 having an acoustic impedance $Z_c$ and the front medium having an acoustic impedance $Z_t$, the impedance of the front layer 16 can be approximated to be between $(Z_c Z_t)^{1/2}$ and $(Z_c Z_t^2)^{1/3}$. For example, for a ceramic impedance of 34 MRayls (for the piezoelectric element 14) and tissue at 1.6 MRayls (for the front medium 18), then it would be desirable for a single quarter wave layer to have an acoustic impedance in the range 4-10 Mrayls.

The front layer 16 can also serve to electrically insulate and/or physically protect the piezoelectric element 14 from physical wear or damage. In some applications, the front layer 16 is also shaped to provide an acoustic lens function to focus ultrasound.

A first implementation of the first conventional ultrasound transducer 10 is shown in FIG. 2 and FIG. 3 to include a housing 22 to enclose components enumerated above. With the first implementation, the piezoelectric element 14 and the front layer 16 are formed and optionally adjusted to project the ultrasound 20 to have a focal point 24 located a desired distance into the front medium 18.

As part of the conversion by the piezoelectric element 14 of electrical energy into ultrasound 20, unwanted heat, as mentioned above, is generated by the piezoelectric element. Electronic compensation can be used with the first conventional ultrasound transducer 10 to help partially mitigate effects of the unwanted heat on performance of the first conventional ultrasound transducer.

A second conventional ultrasound transducer 30 is schematically depicted in FIG. 4 to include a thermal heat sink 32 positioned adjacent to the front layer 16 so that in operation the thermal heat sink is adjacent to the front medium 18 as shown. The thermal heat sink 32 is used to remove heat from the vicinity of the piezoelectric element 14 and is fashioned to conduct the ultrasound 20. Unfortunately, in practice the thermal heat sink 32 can be very thick compared with the front layer 16 along the X-dimension of travel of the ultrasound 20 so can also dissipate significant portions of the ultrasound 20 thereby resulting in more heat being generated and reducing efficiency with the transducer performance. The thermal heat sink 32 can also have other operational issues due to its added size and possible use of fluid, such as water, as at least a portion of the thermal mass.

A first implementation of the second conventional ultrasound transducer 30 is shown in FIG. 5 as using a fluid, such as water, for the thermal heat sink 32, which is shown to be contained by a structural appendage 34 and an acoustic membrane 36. Water can serve a dual purpose to cool and also acoustically couple between the second conventional ultrasound transducer 30 and a target. A second implementation of the second conventional ultrasound transducer 30 is shown in FIG. 6 to include a solid, such as a metal, for the thermal heat sink 32. In this second implementation, the structural appendage 34 includes channels 38 for a fluid, such as water, to be passed through to aid in removal of heat. Associated with these first and second implementations of the second conventional ultrasound transducer 30, the use of fluid, additional mass, attenuation of desired ultrasound energy, and positioning of the thermal heat sink 32 and the structural appendage 34 can raise operational issues.

BRIEF DESCRIPTION OF THE SEVERAL VIEWS OF THE DRAWING(S)

FIG. 34 is a schematic diagram of a monolithic HTC implementation of the piezoelectric element.

FIG. 35 is a schematic diagram of a monolithic HTC implementation of a piezoelectric material.

FIG. 36 is a schematic diagram of a monolithic HTC implementation of a first piezoelectric member.

FIG. 37 is a schematic diagram of a monolithic HTC implementation of a second piezoelectric member.

DETAILED DESCRIPTION OF THE INVENTION

Figure 1:
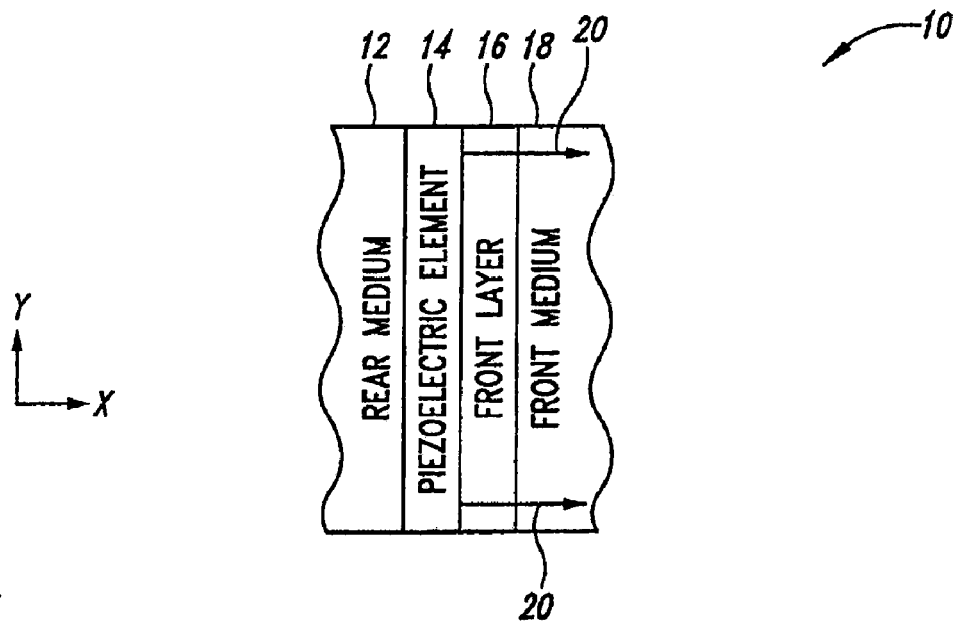
FIG. 1 is a schematic diagram of a first conventional ultrasound transducer.
Figure 2:
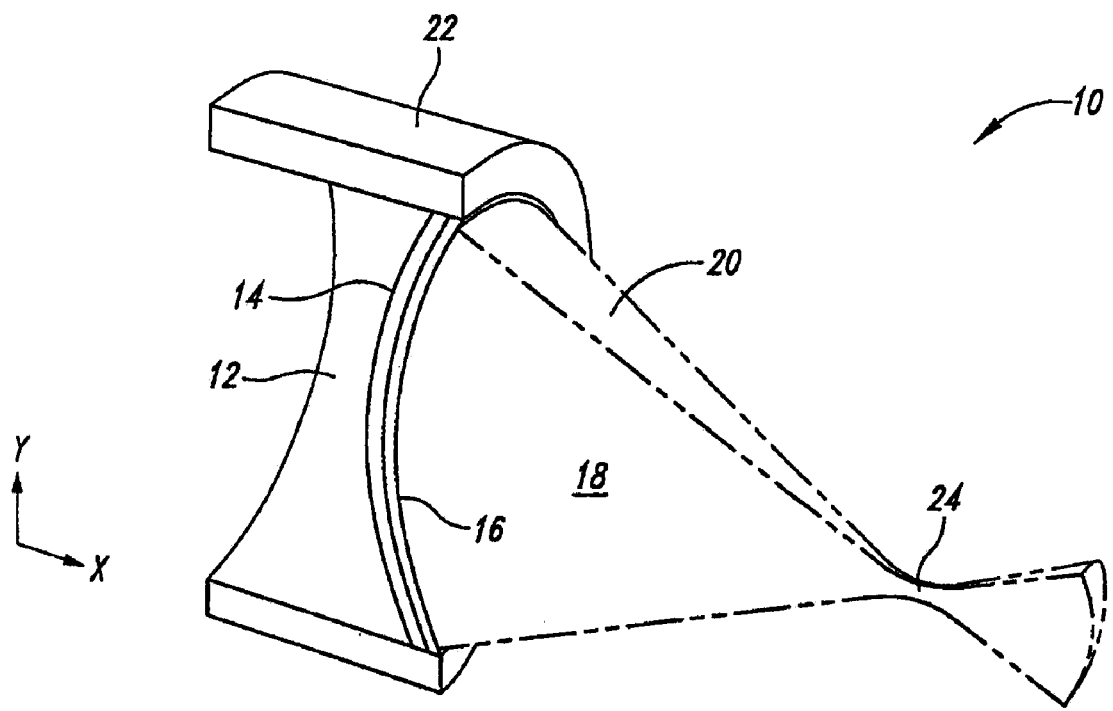
FIG. 2 is a sectional perspective view of a first implementation of the first conventional ultrasound transducer of FIG. 1.
Figure 3:
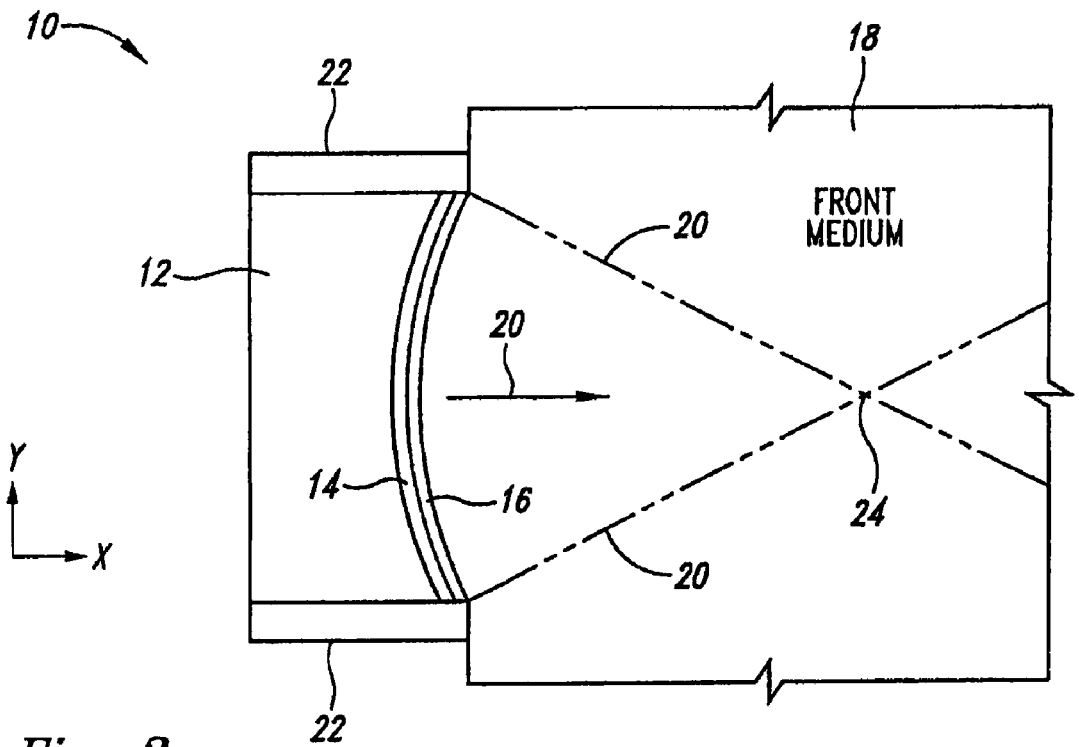
FIG. 3 is a sectional elevation view of the first implementation of the first conventional ultrasound transducer shown in FIG. 2.
Figure 4:
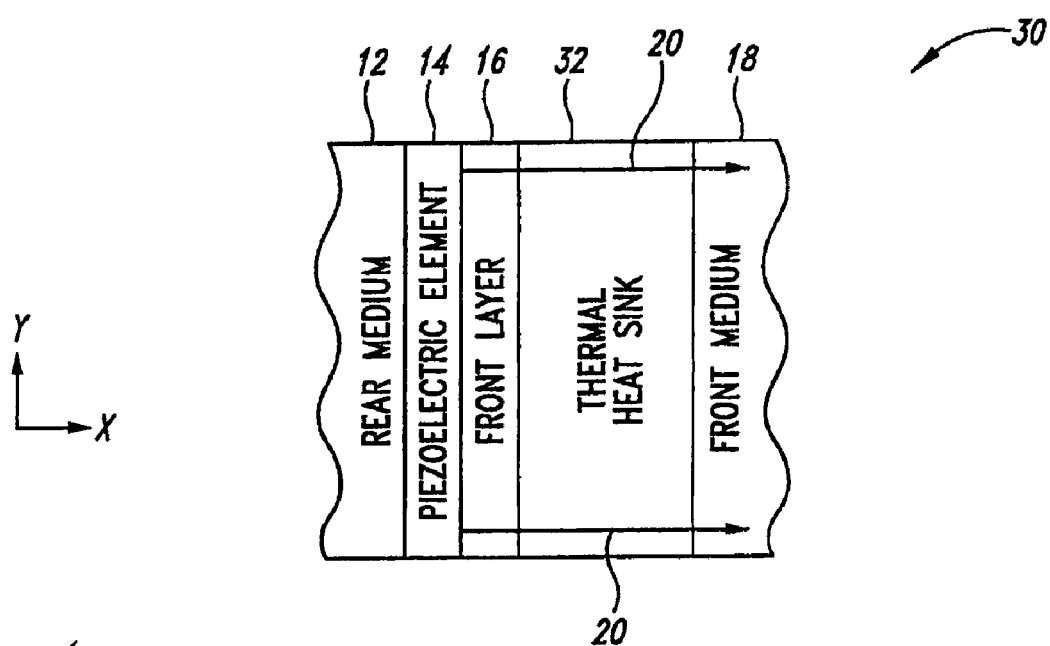
FIG. 4 is a schematic diagram of a second conventional ultrasound transducer.
Figure 5:
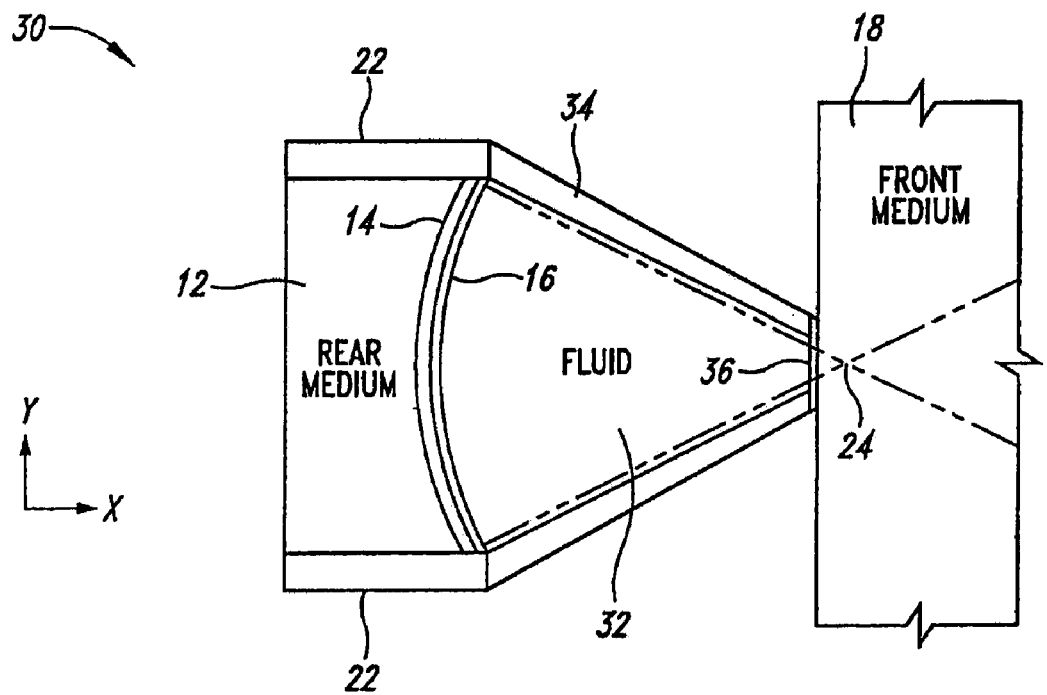
FIG. 5 is a sectional elevation view of a first implementation of the second conventional ultrasound transducer of FIG. 4.
Figure 6:
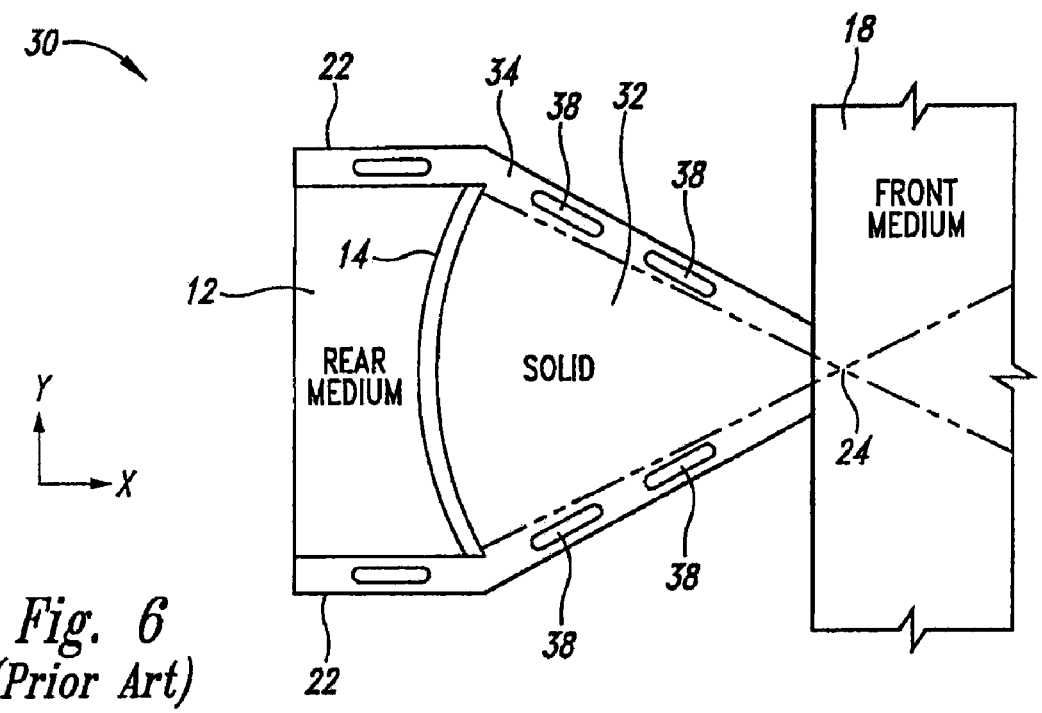
FIG. 6 is a sectional elevation view of a second implementation of the second conventional ultrasound transducer of FIG. 4.

A system and method for removing unwanted heat generated by a piezoelectric element of an ultrasound transducer while maintaining transducer efficiencies is disclosed herein. In some implementations, relatively small amounts of high thermal conductivity (HTC) material are placed in juxtaposition with the piezoelectric element on front and/or back surfaces of the piezoelectric element. Generally HTC materials have a thermal conductivity of over 100 W/mC. Some HTC materials can include metals and other materials of high thermal conductivity (for instance, aluminum at approximately 205-237 W/mC, copper at approximately 385-401 W/mC, gold at approximately 314-318 W/mC, silver at 406-429 W/mC, brass at approximately 109-159 W/mC, impure diamond at approximately 1,000 W/mC, and purified synthetic diamond at approximately 2,000-2,500 W/mC thermal conductivity).

The HTC material can be thermally coupled to one or more heat sinks, which can be integrated with the ultrasound transducer, such as a housing or other structure, and positioned out of the path of ultrasound generated by the piezoelectric element. The typically large surface area versus thickness of the piezoelectric element (for instance, some applications having 50:1 to 100:1) is also used in placement of the HTC material. Use of HTC material in conjunction with these piezoelectric element surfaces is managed to avoid degradation of acoustic energy propagating forward into to a front medium, such as tissue, and to minimize acoustic energy loss through a rear medium.

Piezoelectric ceramic used in HIFU and other transducers is typically coated with a thin (generally less than 10% of an operational ultrasound wavelength) electrically conductive layer to serve as electrodes. This material is also thermally conductive but is purposely relatively thin so that it will have minimal effect on acoustic performance. The present implementations use significantly thicker layers for the HTC material than is typically used for the thin electrically conductive material but not in excess as to degrade transducer efficiency.

Piezoelectric ceramic elements are typically coated with high electrical conductivity material to serve as electrodes on opposite sides of the ceramic. Although the electrode material layer may also have high thermal conductivity, the electrode layer is typically relatively thin, on the order of a few microns, and therefore is limited in its function to transfer heat laterally to a surrounding heatsink. As can be seen in the following equation, the rate of heat transfer by conduction ($\Delta Q/\Delta t$) is a function of the cross section area of the material, A.

$$\frac{\Delta Q}{\Delta t} = \frac{kA\Delta T}{d}$$

where
$\Delta T$=temperature difference
d=length
A=cross-sectional area
k=material thermal conductivity It is preferable to utilize the high thermal conductivity of the electrode layers to conduct heat from the piezoelectric ceramic directly forward and/or backward (in the direction of large cross section area) and into HTC matching layers, such as aluminum. The HTC matching layers have a relatively large cross section area in the lateral direction toward the thermally conductive housing/heatsink due to a thickness that may be 10 to 100 times greater than the electrode thickness.

Use of the HTC material in conjunction with heat sinks allows for creation of thermal paths away from the piezoelectric element so that a thermal gradient is maintained across the span of HTC material and coupled heat sinks. Active cooling of the heat sinks with water or air can further help maintain thermal gradients to draw heat from the piezoelectric element. Various applications include continuous run times of several minutes (with a minimum of at least a few seconds) in which high levels of ultrasound are generated and transmitted into target tissue without significant loss of acoustic energy and without thermal damage to associated equipment or thermal based injury occurring. In some cases, it is desirable to utilize a transducer of relatively small size, driven at a relatively high acoustic power, which makes further demands on the thermal management of the transducer system.

Further implementations improve the thermal conductivity of the piezoelectric element itself by forming a composite matrix of thermally conductive material or by interleaving the ceramic with thermally conductive layers. Increased thermal conductivity of the piezoelectric element helps to move thermal energy toward outside edges and/or front and back surfaces.

Figure 7:
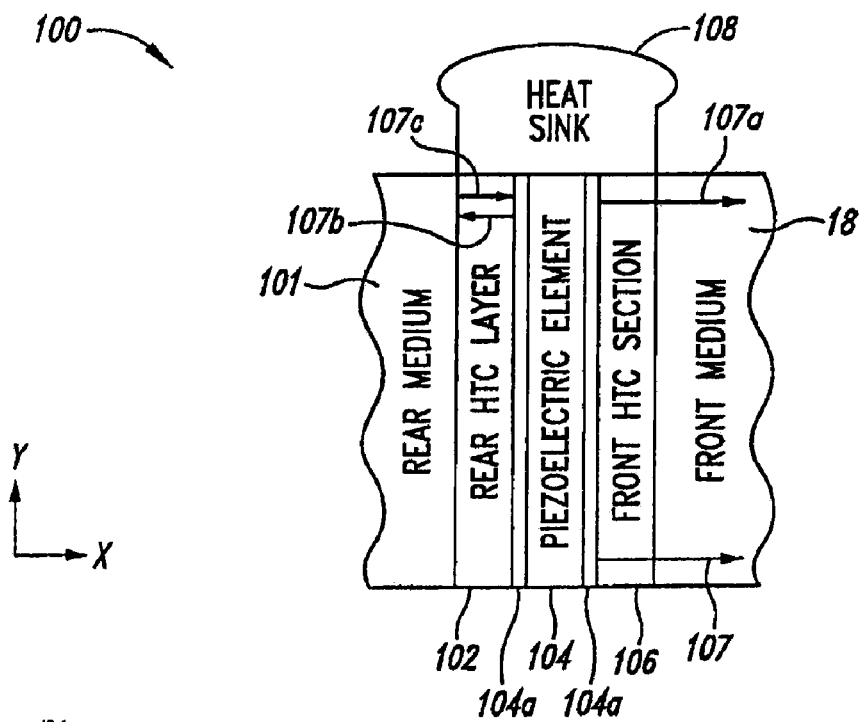
FIG. 7 is a schematic diagram of a first implementation of a thermally enhanced ultrasound transducer.

A first implementation of a thermally enhanced ultrasound transducer 100 is shown in FIG. 7 to include a rear medium 101, such as air, positioned adjacent to a rear high thermal conductivity (HTC) layer 102. In contrast, if the rear medium 101 is water rather than the air, the reflected wave is reduced to approximately 84%, which can be unacceptable for some applications. In general, a member, a layer, a material, an element, a section, or other portion of the thermally enhanced ultrasound transducer 100 designated herein as "high thermal conductivity (HTC)," the thermal conductivity of such portion is substantially similar or higher than metals such as aluminum unless such portion is formed as a composite such as a polymer with metal powder as further described below.

It is desired that negligibly small amounts of acoustic energy should be absorbed by the rear HTC layer 102 and thus low acoustic absorption materials such as a metal, which also has a high thermal conductivity, is most desirable. In turn, the rear HTC layer 102 is positioned in juxtaposition with a piezoelectric element 104, which is positioned in juxtaposition with a front high thermal conductivity (HTC) section 106. The piezoelectric element 104 is shown in FIG. 7 to be positioned between and adjacent to electrode material 104a, which is adjacent to the rear HTC layer 102 and the front HTC section 106. The electrode material 104a is typically a few microns thick of electrically conductive material. Because the electrode material 104a is electrically conductive, the electrode material is also thermally conductive. The electrode material 104a is made purposely thin such as typically small fractions of a wavelength so that there will be minimal effect on the acoustic performance.

In contrast, with 4 MHz resonance frequency ultrasound production, the rear HTC layer 102 has a thickness in the range of hundreds of microns as determined by the particular resonance frequency being used and without significantly degrading transducer efficiency. The piezoelectric element 104 can be made from ceramics such as lead titanates and lead zirconate titanates or other materials that have a piezoelectric effect.

The piezoelectric element 104 generates forward ultrasound 107a and rearward ultrasound 107b. Due to the discontinuity between the rear medium 101 and the layer in juxtaposition (the rear HTC layer 102 as depicted in FIG. 7 or the piezoelectric element 104 in other implementations), a portion of the rearward ultrasound 107b reverses direction as reflected ultrasound 107c to add constructively with the forward ultrasound 107a as combined ultrasound 107. In implementations the rear medium 101 can typically be comprised of air so that nearly all of the rearward ultrasound 107b reverses direction as the reflected 107c due to a large difference between acoustic impedances between the rear medium 101 and the layer in juxtaposition (the rear HTC layer 102 as depicted in FIG. 7 or the piezoelectric element 104 in other implementations).

The polarity of the reflected ultrasound 107c depends upon the relative acoustic impedances of the rear medium 101 and the layer in juxtaposition (the rear HTC layer 102 as depicted in FIG. 7 or the piezoelectric element 104 in other implementations). If the acoustic impedance of the rear medium 101 is low (such as for air) relative to the acoustic impedance of the layer in juxtaposition, which has a relatively high acoustic impedance (such as aluminum for the rear HTC layer 102 depicted in FIG. 7 or ceramic for the piezoelectric element 104 for other implementations), then the reflected ultrasound 107c will have opposite polarity than the rearward ultrasound 107b. As a result the reflected ultrasound 107c will travel back toward the piezoelectric element in phase and will interfere constructively with forward ultrasound 107a as both the forward ultrasound 107a and the reflected ultrasound 107c will propagate to the front medium 18 is a desired configuration such as a HIFU beam. Conversely, the reflected ultrasound 107c has the same polarity as the rearward ultrasound 107b if the acoustic impedance of the rear medium 101 is high relative to the layer in juxtaposition.

In an implementation, the rearward ultrasound 107b propagates first from the piezoelectric element 104 through the rear HTC layer 102 made from aluminum to the rear medium 101 comprised of air. A reflection coefficient can be calculated at the boundary between air and the top side of an aluminum version of the rear HTC layer 102 by substituting $Z_2$ for the impedance of air (0.000411 MRayls) and $Z_1$ for aluminum (17.1 MRayls) in equation (1) as shown in equation (2) as follows:

$$r = \frac{411 * 10^{-6} - 17.1}{411 * 10^{-6} + 17.1} \cong -1.0 \tag{2}$$

Showing that reflection of the rearward ultrasound 107b can be close to complete.

Implementations include thicknesses dependent upon the selected operational frequency such as the nominal center ultrasound frequency for the rear HTC layer 102 of one or more multiples of approximately one half wavelength at the nominal center ultrasound frequency (for example, approximately 0.8 mm for a nominal center frequency of 4 MHz). In implementations constructive reflection of the rearward ultrasound 107b is attained if the rear HTC layer 102 is a single or a multiple of half ultrasound wavelengths at the nominal center ultrasound frequency. However, the rear HTC layer 102 will be too thick having a thickness of too many multiples of the one half wavelength if an undesirable amount of acoustic energy from the rearward ultrasound 107b is absorbed by the rear HTC layer as the rearward ultrasound is being reflected. In some implementations a single half wavelength thickness is used as a compromise between a too thick heat sink that would absorb too much acoustic energy and a too thin heat sink that would not remove enough thermal energy.

The rear HTC layer 102 has high thermal conductivity such as provided by aluminum or other metal-based material (much higher than piezoelectric material, such as at least greater than 100 W/mC for implementations) to enable its use as a thermal pathway for extracting the heat from the piezoelectric element 104 directly to the rear medium 101 (such as air). Also, using air or other substance with a similar acoustic impedance for the rear medium 101 allows the rearward ultrasound 107b to be mostly reflected as the reflected ultrasound 107c.

The front HTC section 106 is to be positioned adjacent to the front medium 18 so that the combined ultrasound 107 will travel through the front HTC section 106 on into the front medium 18. The first implementation of the transducer 100 further includes a heat sink 108 that is thermally coupled to and substantially extending along the illustrative Y-dimension away from the rear HTC layer 102, coupled to and extending along the illustrative Y-dimension away from the piezoelectric element 104, and coupled to and extending along the illustrative Y-dimension away from the front HTC section 106 to increase effectiveness of heat removal from the piezoelectric element 104 while staying out of direct travel of the ultrasound 107 along the illustrative X-dimension so as not to diminish ultrasound levels reaching the front medium 18. As depicted below, although other implementations of the heat sink 108 include various segmentation, the heat sink 108 remains out of travel of the ultrasound 107 along the illustrative X-dimension. In general, thermal paths with large thermal gradients are used to draw heat rapidly away from the piezoelectric element 104 to one or more heat sinks, which are typically relatively large masses (several times that of the piezoelectric element 104) of thermally conductive material.

The heat sink 108 can take the form of a fluid, such as water (circulating or stationary) and/or a solid material including housing structures (for example, as housing 108a shown below in FIG. 8) of the thermally enhanced ultrasonic transducer 100. Heat removal can be further enhanced by active cooling of the heat sink 106 such as by other circulating water or air through or around a solid version of the heat sink. For instance, water can be circulated through the front HTC section 106 of the transducer; for smaller heat removal requirements, air can be used, which can be more desirable since air has less contamination concerns and generally can have less practical obstacles to implement than when water is used. Once the heat is removed from the front HTC section 106, the heat is further removed from the circulating fluid through use of one or more heat sinks to transfer heat from the fluid to surrounding air.

In implementations one or more portions or instances of the heat sink 108 are located in peripheral locations out of the path of the forward ultrasound 107a, rearward ultrasound 107b, reflected ultrasound 107c and the combined ultrasound 107. The rear HTC layer 102 and/or the front HTC section 106 can be press-fit, and/or bonded using thermally conductive adhesive, and/or soldered, and/or integrally formed with other structures like a housing portion of the thermally enhanced ultrasonic transducer 100 such as aluminum.

In some implementations the front HTC section 106 is thermally coupled but electrically isolated to the heat sink 108 such as a housing structure of the thermally enhanced ultrasonic transducer 100 so that the housing structure can also be thermally coupled and electrically coupled to the face of the piezoelectric element facing the rear medium 101 or coupled to the rear HTC layer 102 without creating an electrical short circuit. Alternatively, the front HTC section 106 may be both electrically and thermally coupled to the heat sink 108 and the rear HTC layer 102 may be thermally coupled and electrically isolated from the heat sink 108. Generally, thermal coupling is of a sufficient heat flux to prevent significant elevation of temperature and to prevent consequential diminished ultrasound output. In other words, thermal pathways used to remove heat can scale to the amount of heat generated by the piezoelectric element 104 so that if heat output increases the thermal pathways have reserve capacity to remove the increases in generated heat.

Figure 8:
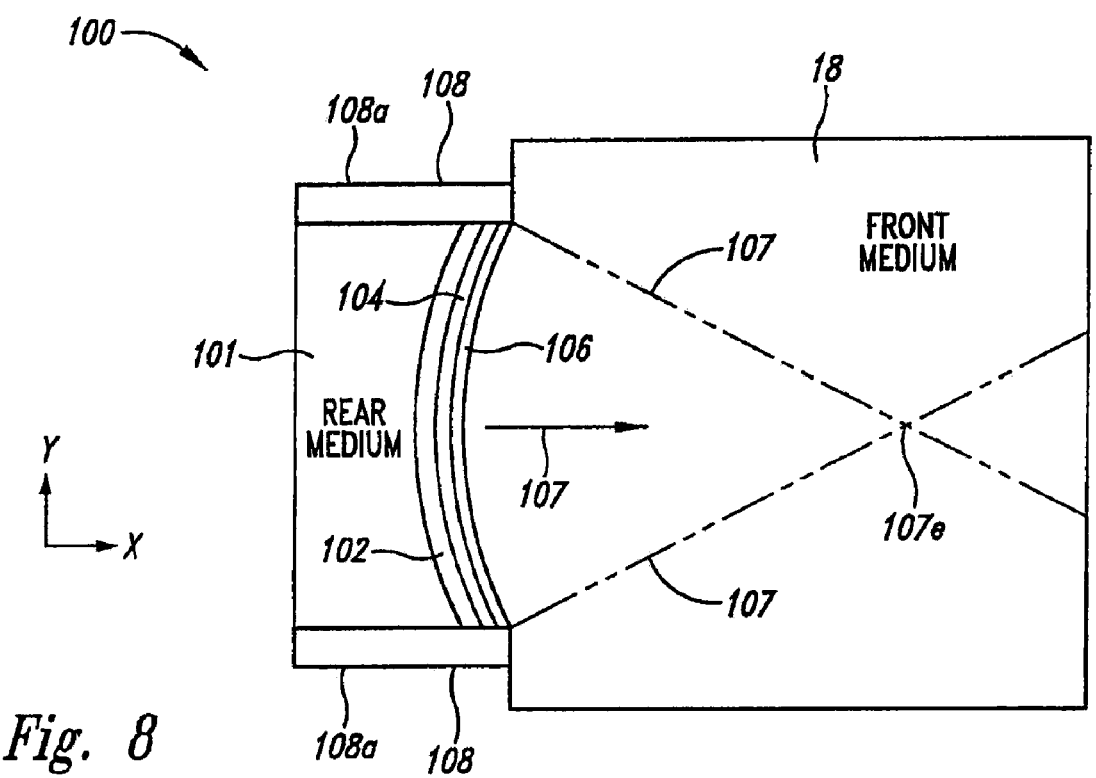
FIG. 8 is a sectional elevation view of a first variation of the first implementation of the thermally enhanced ultrasound transducer shown in FIG. 7.

A first variation of the first implementation of the thermally enhanced ultrasound transducer 100 is shown in FIG. 8 in which the rear HTC layer 102, the piezoelectric element 104, and the front HTC section 106 are all curved to allow for focusing of the combined ultrasound 107 at a focal point 107e.

Figure 9:
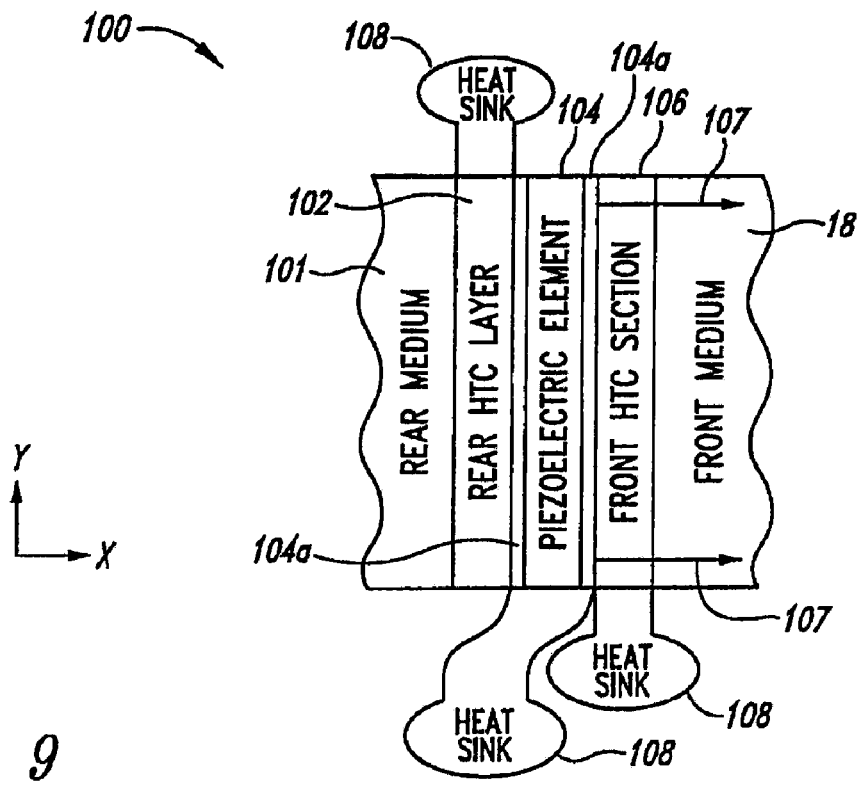
FIG. 9 is a schematic diagram of a second implementation of the thermally enhanced ultrasound transducer.

A second implementation of the thermally enhanced ultrasound transducer 100 is shown in FIG. 9 in which the rear HTC layer 102, the piezoelectric element 104, and the front HTC section 106 are each thermally coupled to different instances of the heat sink 108.

Figure 10:
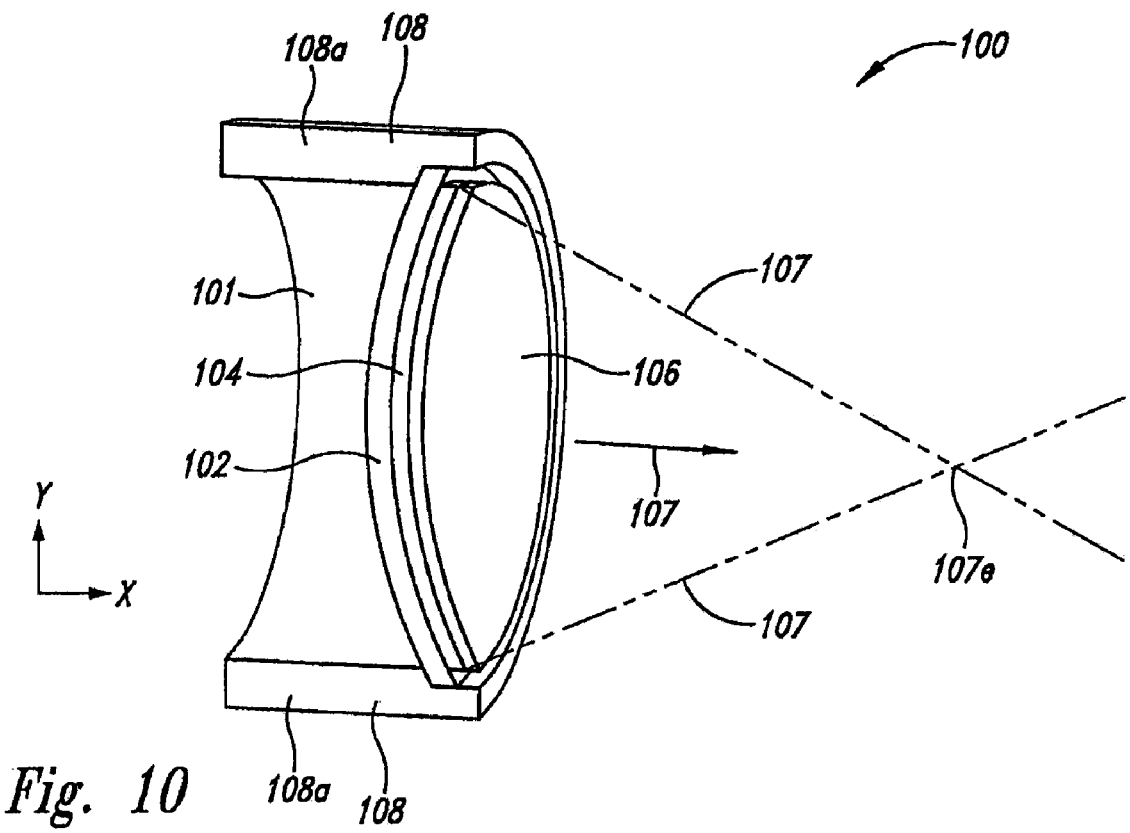
FIG. 10 is a sectional perspective view of a first variation of the second implementation of the thermally enhanced ultrasound transducer shown in FIG. 9.

A first variation of the second implementation of the thermally enhanced ultrasound transducer 100 is shown in FIG. 10 in which only the rear HTC layer 102 is directly coupled to an instance of the heat sink 108. Although this implementation is depicted with the piezoelectric element 104 as being round in shape, other implementations of the thermally enhanced ultrasound transducer 100 have other geometric shapes including rectangular and elliptical.

In this first variation, heat from the piezoelectric element 104 and the front HTC section 106 is transferred through the rear HTC layer 102 on to the instance of the heat sink 108 that is directly coupled to the rear HTC layer. Furthermore, in this first variation, the rear HTC layer 102, the piezoelectric element 104, and the front HTC section 106 are substantially spherically or semi-spherically shaped to allow for focusing of the combined ultrasound 107 having a beam pattern with the focal point 107e. Other implementations use focusing schemes such as the piezoelectric element 104 being aspherically shaped and/or with an acoustic lens applied in front of the piezoelectric element.

Figure 11:
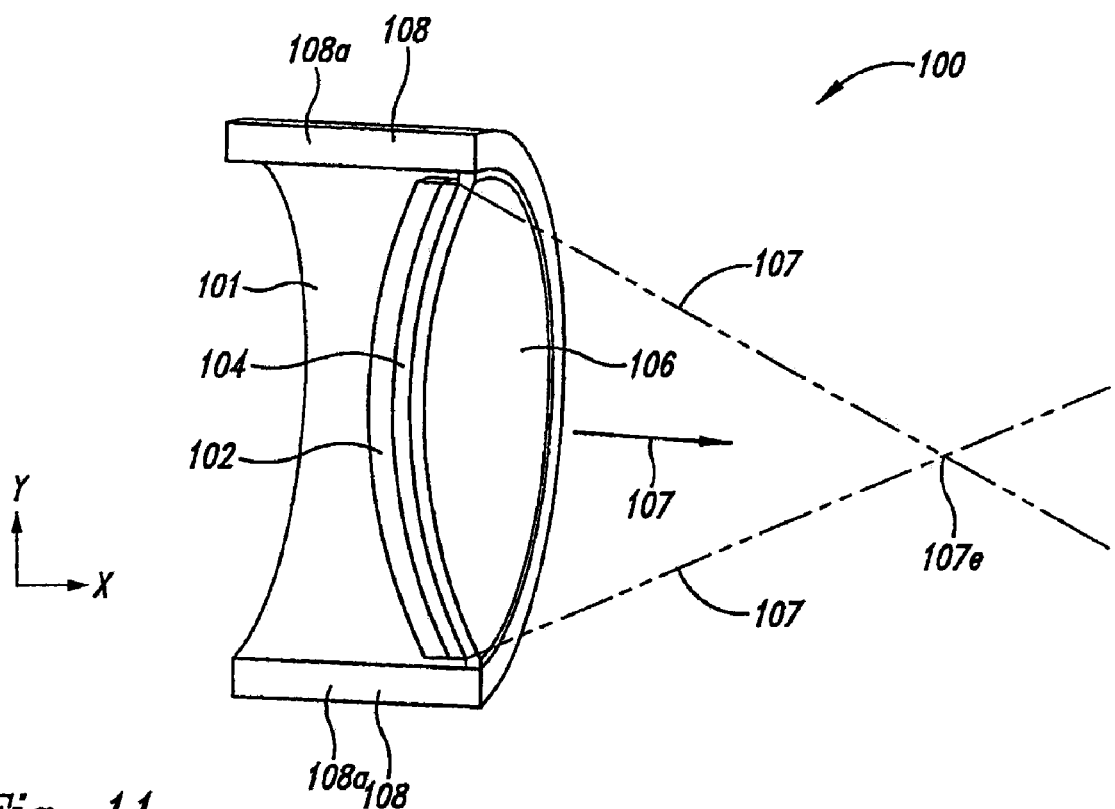
FIG. 11 is a sectional perspective view of a second variation of the second implementation of the thermally enhanced ultrasound transducer shown in FIG. 9.

A second variation of the second implementation of the thermally enhanced ultrasound transducer is shown in FIG. 11 in which only the front HTC section 106 is directly coupled to an instance of the heat sink 108. In this second variation, heat from the rear HTC layer 102 and the piezoelectric element 104 is transferred through the front HTC section 106 on to the instance of the heat sink 108 that is directly coupled to the front HTC section. Furthermore, in this second variation, the rear HTC layer 102, the piezoelectric element 104, and the front HTC section 106 are all semi-spherically formed as curved to allow for focusing of the combined ultrasound 107 with respect to the focal point 107e.

Figure 12:
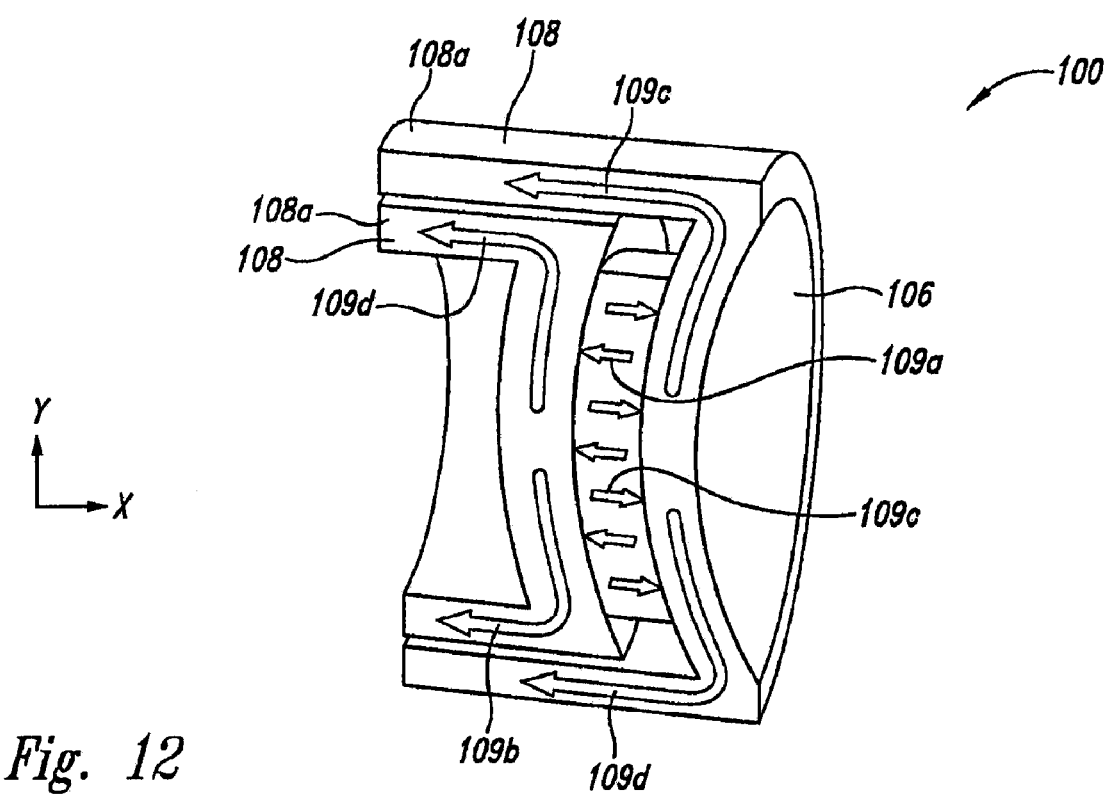
FIG. 12 is a sectional perspective view of a third variation of the second implementation of the thermally enhanced ultrasound transducer shown in FIG. 9.

A third variation of the second implementation of the thermally enhanced ultrasound transducer is shown in FIG. 12 in which the rear HTC layer 102 integrated with an instance of the heat sink 108 and the front HTC section 106 is integrated with another different instance of the heat sink 108. The rear HTC layer 102 and the front HTC section 106 are directly integrated with different instances of the heat sink 108 to remain electrically isolated from one another. In this third variation, the piezoelectric element 104 is not directly thermally coupled to an instance of the heat sink 108. Instead, heat 109a from the piezoelectric element 104 is transferred through the rear HTC layer 102 as heat 109b and heat 109c through the front HTC section 106 as heat 109d on to the instances of the heat sink 108.

Figure 13:
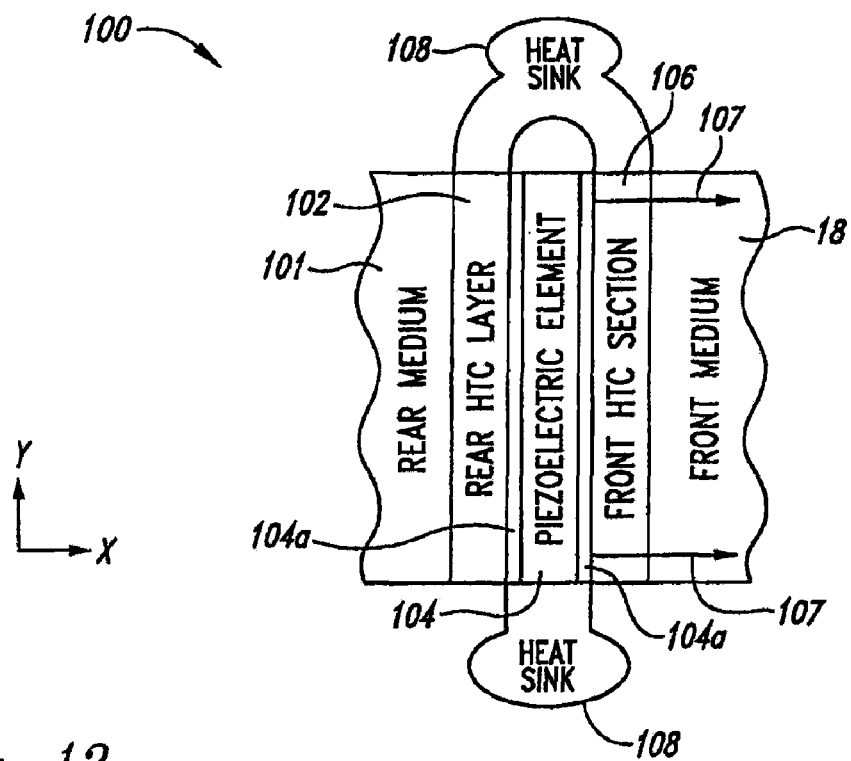
FIG. 13 is a schematic diagram of a third implementation of the thermally enhanced ultrasound transducer.

A third implementation of the thermally enhanced ultrasound transducer 100 is shown in FIG. 13 in which the rear HTC layer 102 and the front HTC section 106 are thermally coupled to an instance of the heat sink 108 and the piezoelectric element 104 is thermally coupled to a different instance of the heat sink.

Figure 14:
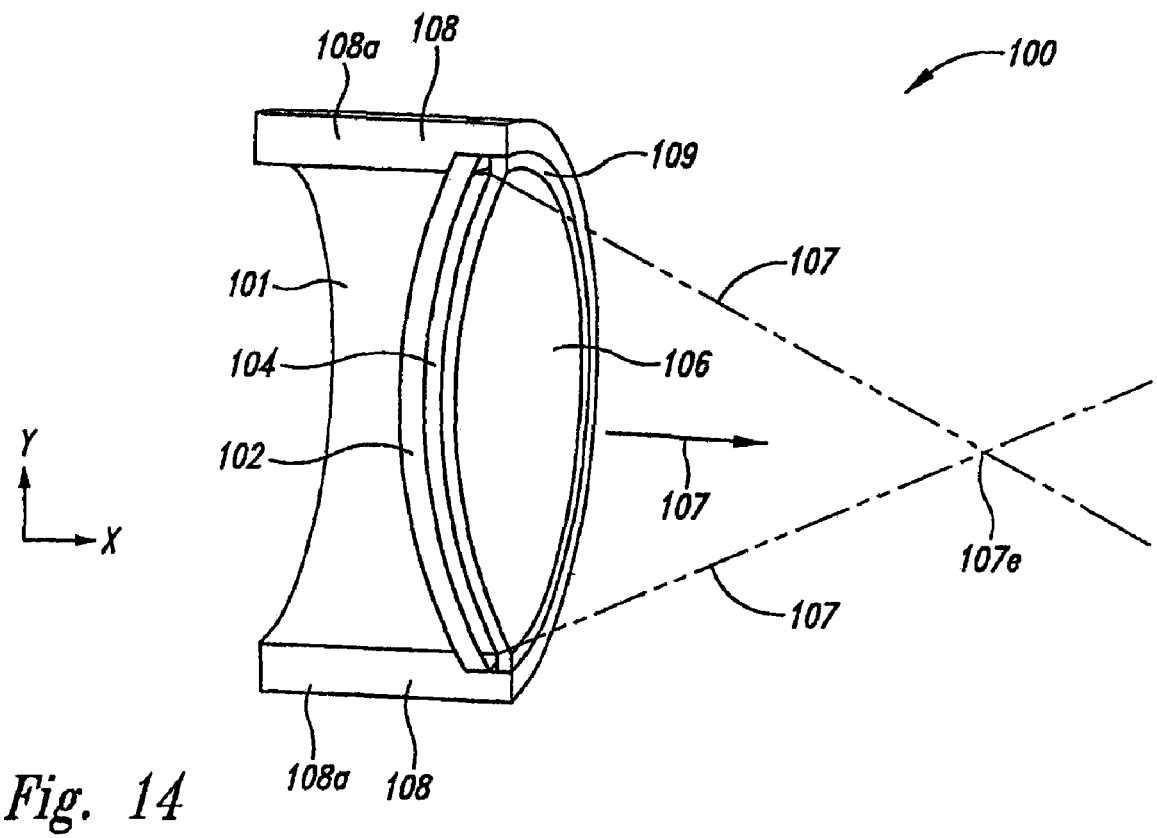
FIG. 14 is a sectional perspective view of a first variation of the third implementation of the thermally enhanced ultrasound transducer shown in FIG. 13.

A first variation of the third implementation of the thermally enhanced ultrasound transducer 100 is shown in FIG. 14 in which the rear HTC layer 102 is thermally and electrically coupled directly to an instance of the heat sink 108 and the front HTC section 106 is thermally coupled to the instance of the heat sink through an electrical isolator 109 to remain electrically isolated from one another. In this first variation, heat from the piezoelectric element 104 is transferred through the rear HTC layer 102 and through the front HTC section 106 on to the instance of the heat sink 108.

Figure 15:
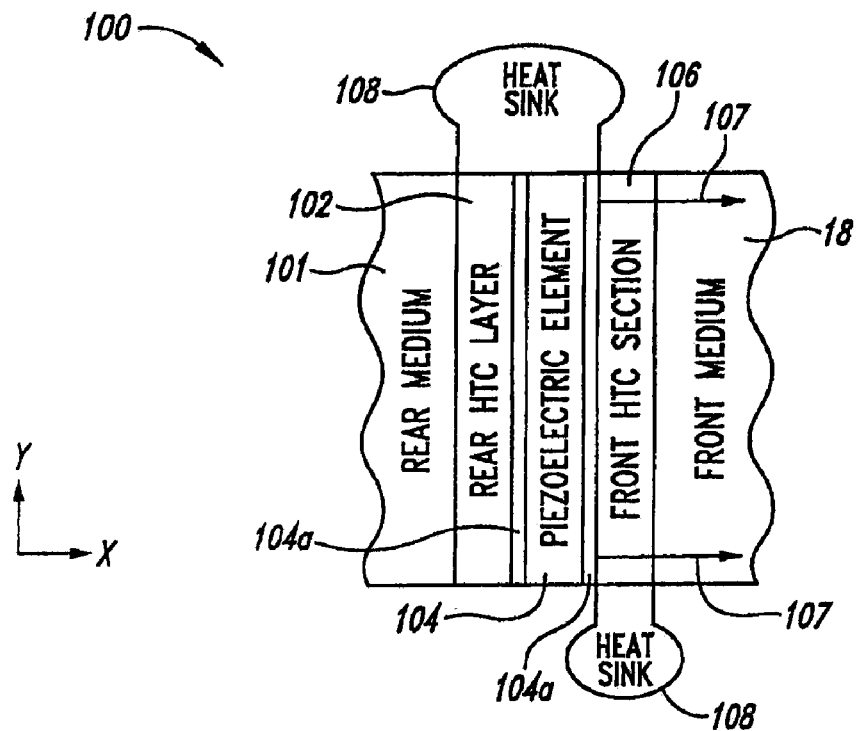
FIG. 15 is a schematic diagram of a fourth implementation of the thermally enhanced ultrasound transducer.

A fourth implementation of the thermally enhanced ultrasound transducer 100 is shown in FIG. 15 in which the rear HTC layer 102 and the piezoelectric element 104 are both thermally coupled to an instance of the heat sink 108. Also, the front HTC section 106 is thermally coupled to another different instance of the heat sink 108.

Figure 16:
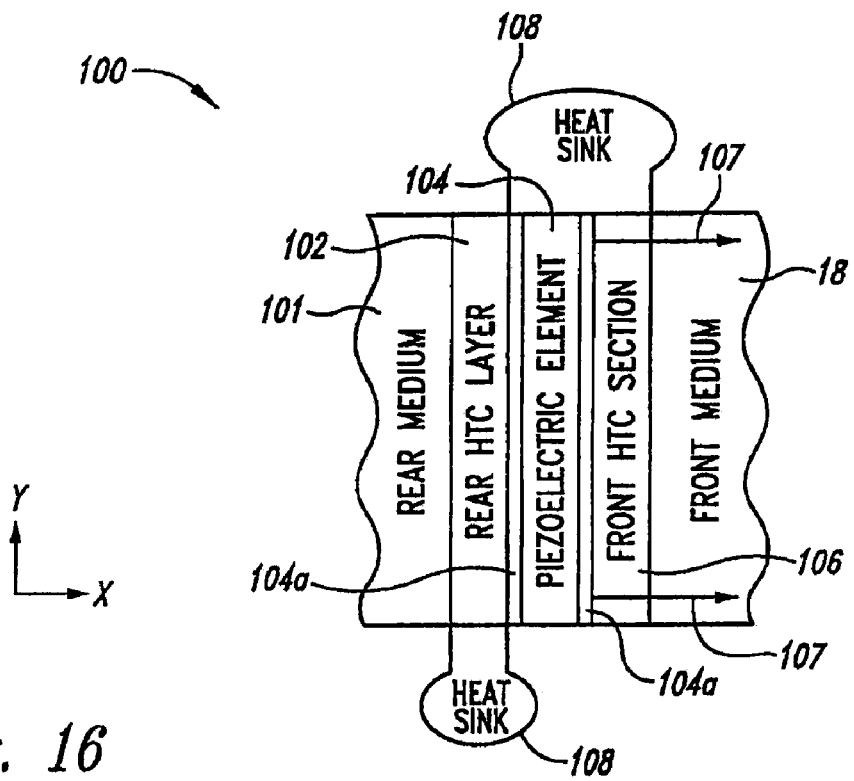
FIG. 16 is a schematic diagram of a fifth implementation of the thermally enhanced ultrasound transducer.

A fifth implementation of the thermally enhanced ultrasound transducer 100 is shown in FIG. 16 in which the rear HTC layer 102 is thermally coupled to an instance of the heat sink 108. Also, the piezoelectric element 104 and the front HTC section 106 are both thermally coupled to another different instance of the heat sink 108.

Figure 17:
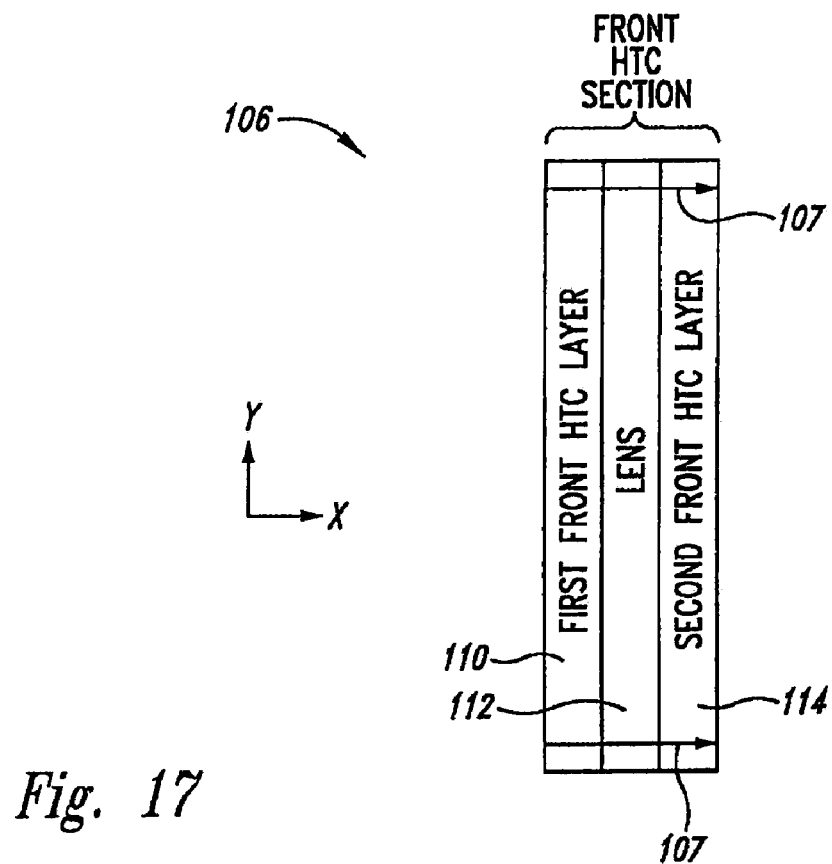
FIG. 17 is a schematic diagram of a first version of the front high thermal conductivity (HTC) section of the thermally enhanced ultrasound transducer.

A first version of the front HTC section 106 is shown in FIG. 17 as having a first front HTC layer 110, an acoustic lens 112, and a second front HTC layer 114. Both the first front HTC layer 110 and the second front HTC layer 114 can be approximately as thick as one or more quarters of a wavelength near the nominal center frequency of the operational ultrasound. For example, for a ceramic version of the piezoelectric element 104 having an acoustic impedance of 34 MRayls and a tissue version of the front medium 18 having an acoustic impedance of 1.6 MRayls, some implementations of the first front HTC layer 110 and the second front HTC layer 114 each of a quarter wave thickness have an acoustic impedance in the range 4 to 10 MRayls. The first front HTC layer 110 and the second front HTC layer 114 can be constructed from magnesium with an acoustic impedance of 10 MRayls or an epoxy filled with a thermally conductive material to yield an acoustic impedance of approximately 7 MRayls.

The acoustic lens 112 is positioned between the first front HTC layer 110 and the second front HTC layer 114. The acoustic lens 112 can also be constructed from a high thermal conductivity material (such as in the range of 200-400 W/mC) and assist in removing heat away from the piezoelectric element 104. As discussed below, the acoustic lens 112 may be utilized without one or both of the first front HTC layer 110 and the second front HTC layer 114, however, generally heat removal from the piezoelectric element 104 can be greater if one or both of the first HTC layer and the second front HTC layer are used in conjunction with an HTC constructed acoustic lens.

Additional factors involved with whether to combine the first front HTC layer 110 and/or the second front HTC layer 114 with the acoustic lens 112 may depend at least in part on acoustic impedances associated with each component and the front medium 18 regarding transducer efficiency. In some implementations the acoustic lens 112 can be made from aluminum with a high thermal conductivity of approximately 237 W/mC. As discussed further below, the acoustic lens 112 can be bonded directly to the piezoelectric element 104 or the first front layer HTC 110. As shown, the combined ultrasound 107 passes through the first front HTC layer 110, then passes through the acoustic lens 112, and finally passes through the second front HTC layer 114.

Figure 18:
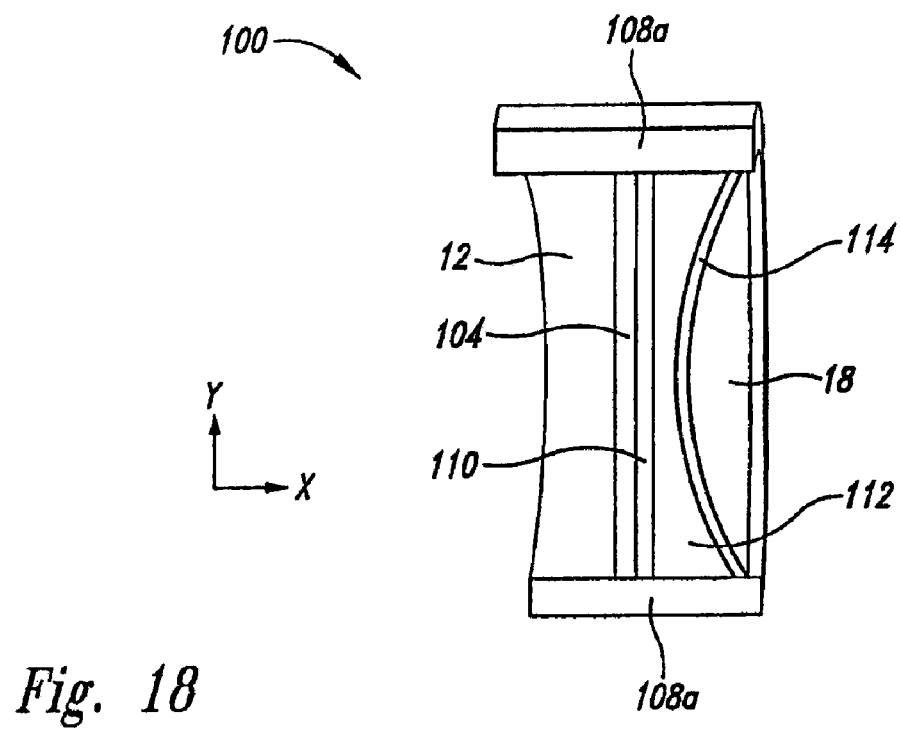
FIG. 18 is a sectional perspective view of a first variation of the fifth implementation of the thermally enhanced ultrasound transducer using the first version of the front HTC section.

A first variation of the fifth implementation of the thermally enhanced ultrasound transducer 100 is shown in FIG. 18 as using the first version of the front HTC section 106.

Figure 19:
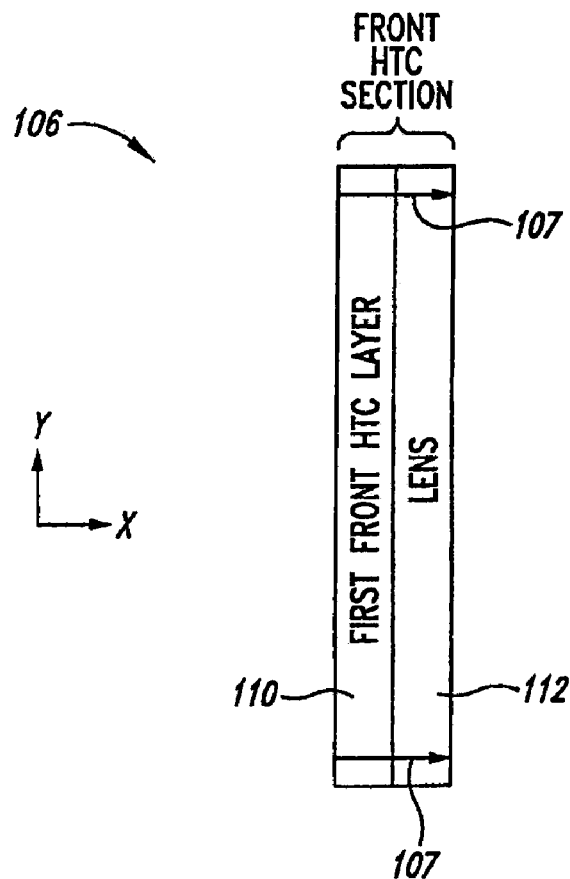
FIG. 19 is a schematic diagram of a second version of the front high thermal conductivity (HTC) section of the thermally enhanced ultrasound transducer.

A second version of the front HTC section 106 is shown in FIG. 19 as having the first front HTC layer 110 adjacent to the acoustic lens 112. As shown, the combined ultrasound 107 passes through the first front HTC layer 110 and then passes through the acoustic lens 112.

Figure 20:
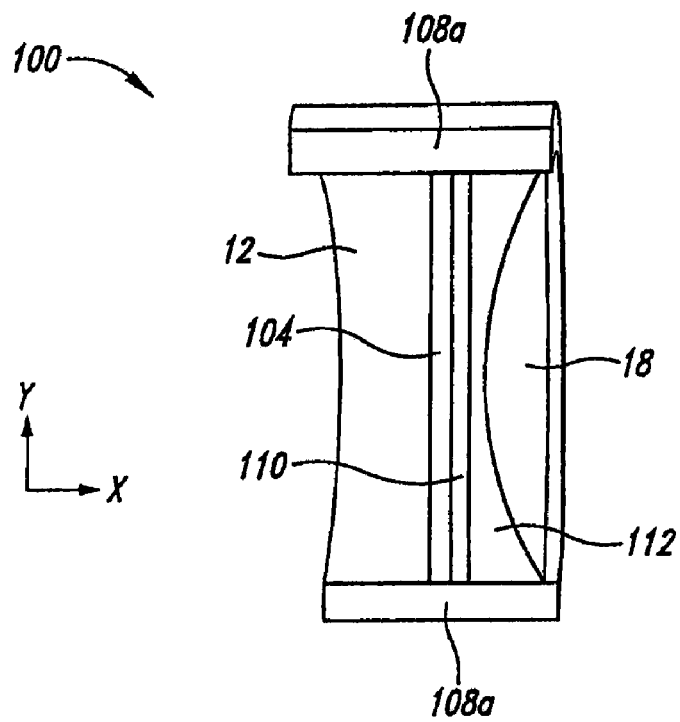
FIG. 20 is a sectional perspective view of a second variation of the fifth implementation of the thermally enhanced ultrasound transducer using the second version of the front HTC section.

A second variation of the fifth implementation of the thermally enhanced ultrasound transducer 100 is shown in FIG. 20 as using the second version of the front HTC section 106.

Figure 21:
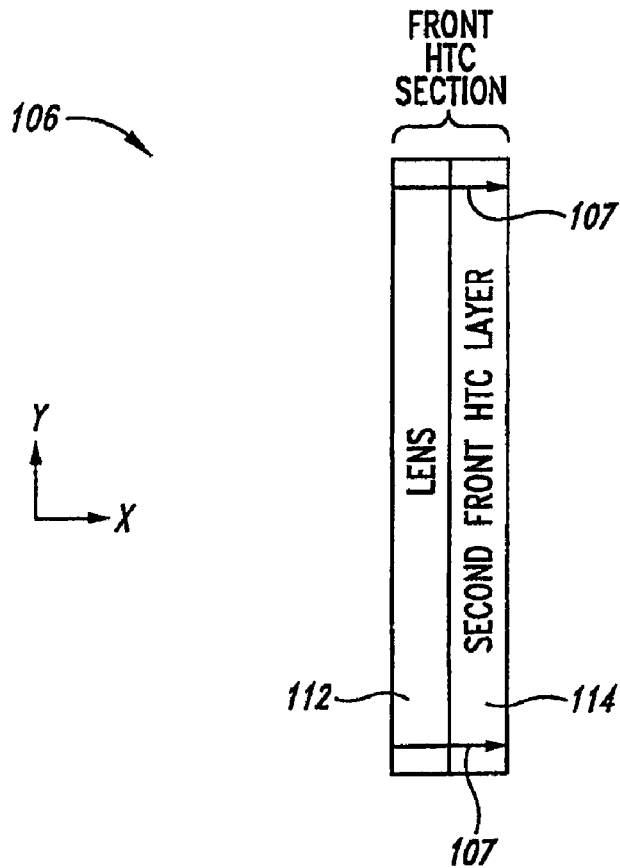
FIG. 21 is a schematic diagram of a third version of the front high thermal conductivity (HTC) section of the thermally enhanced ultrasound transducer.

A third version of the front HTC section 106 is shown in FIG. 21 as having the acoustic lens 112 and the second front HTC layer 114. As shown, the combined ultrasound 107 passes through the acoustic lens 112 and then passes through the second front HTC layer 114.

Figure 22:
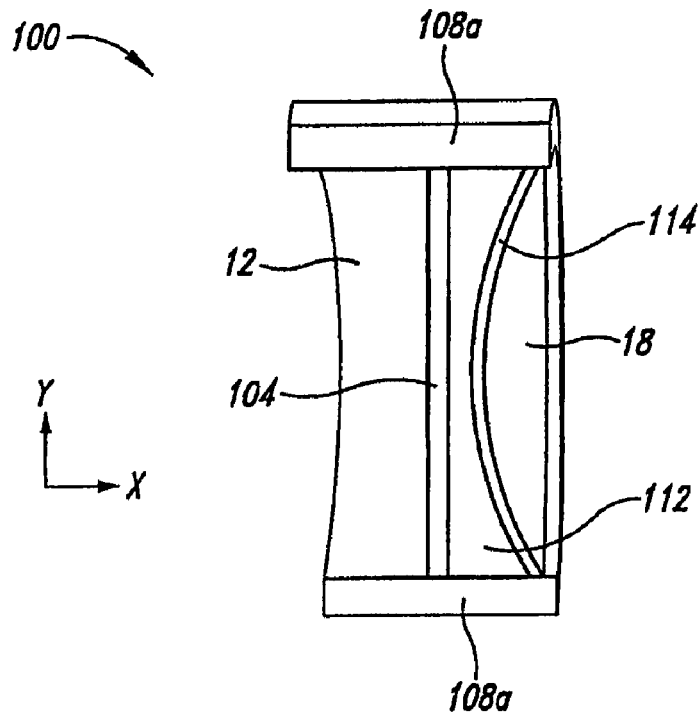
FIG. 22 is sectional perspective view at a third variation of the fifth implementation of the thermally enhanced ultrasound transducer using the third version of the front HTC section.

A third variation of the fifth implementation of the thermally enhanced ultrasound transducer 100 is shown in FIG. 22 as using the third version of the front HTC section 106.

Figure 23:
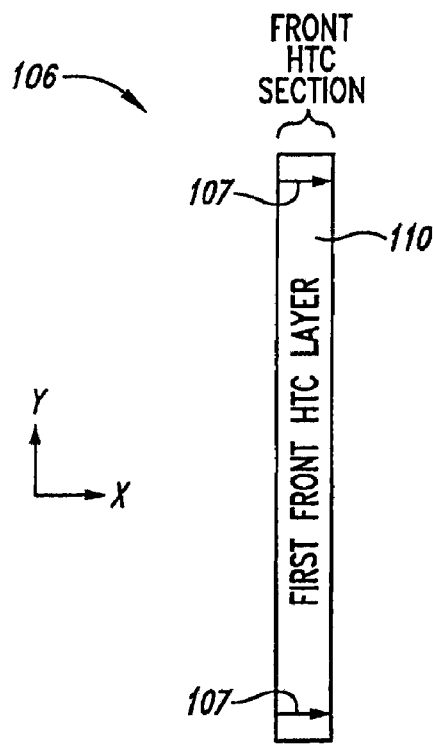
FIG. 23 is a schematic diagram of a fourth version of the front high thermal conductivity (HTC) section of the thermally enhanced ultrasound transducer.

A fourth version of the front HTC section 106 is shown in FIG. 23 as having the first front HTC layer 110. As shown, the combined ultrasound 107 passes through the first front HTC layer 110.

Figure 24:
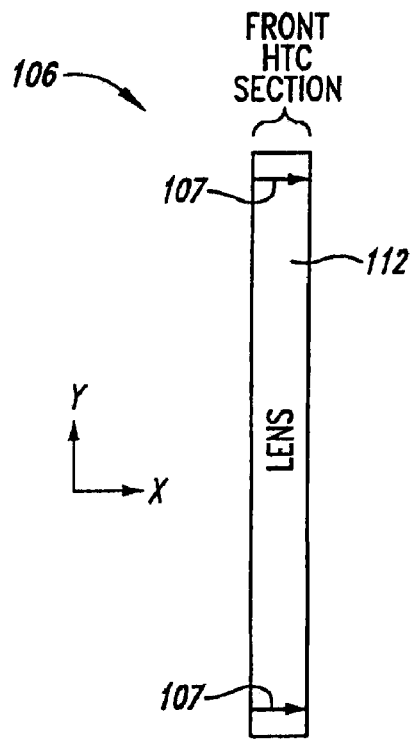
FIG. 24 is a schematic diagram of a fifth version of the front high thermal conductivity (HTC) section of the thermally enhanced ultrasound transducer.
Figure 25:
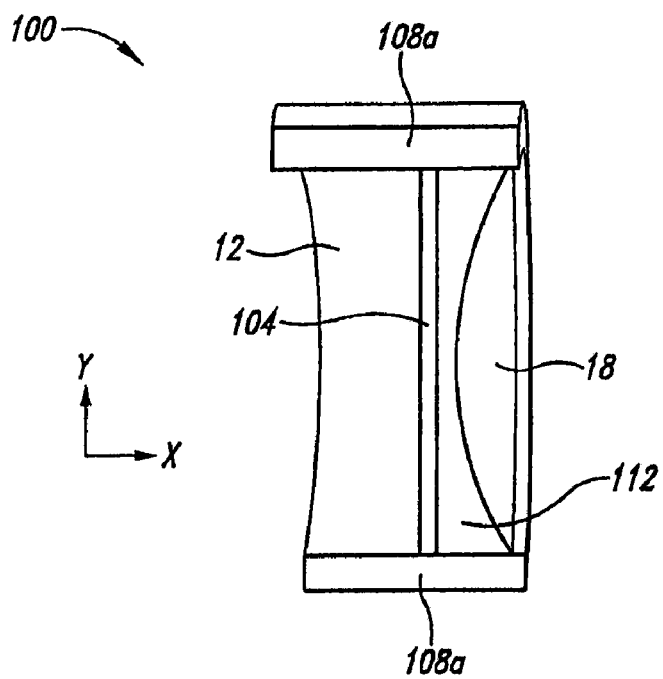
FIG. 25 is sectional perspective view at a fourth variation of the fifth implementation of the thermally enhanced ultrasound transducer using the fifth version of the front HTC section.

A fifth version of the front HTC section 106 is shown in FIG. 24 as having the acoustic lens 112. As shown, the combined ultrasound 107 passes through the acoustic lens 112.

A fourth variation of the fifth implementation of the thermally enhanced ultrasound transducer 100 is shown in FIG. 22 as using the fifth version of the front HTC section 106.

Implementations of the thermally enhanced ultrasound transducer 100 can also include enhancements to the piezoelectric element 104 to increase thermal conduction within the piezoelectric element. Bulk thermal conductivity of the piezoelectric element 104 can be increased by forming a composite matrix of thermal conductive material (such as some epoxies and/or epoxies mixed with high thermal conductivity material such as metals) and piezoelectric material (such as ceramics).

Bulk piezoelectric element thermal conductivity can also be increased by interleaving ceramic material (such as ceramics) with thermally conductive layers (such as metals). Effective distances can be consequently shortened within the piezoelectric element 104 from ceramic material within the piezoelectric element to thermal conductive pathways within the piezoelectric element coupled to one or more thermal conductive pathways and/or one or more instances of the heat sink 108 external to the piezoelectric element. External thermal conductive pathways can include the rear HTC layer 102 and the front HTC section 106. Thermal conductive pathways internal to the piezoelectric element 104 can conduct heat away from piezoelectric material to various external surfaces of the piezoelectric element, external thermal conductive pathways, and one or more instances of the heat sink 108.

Figure 26:
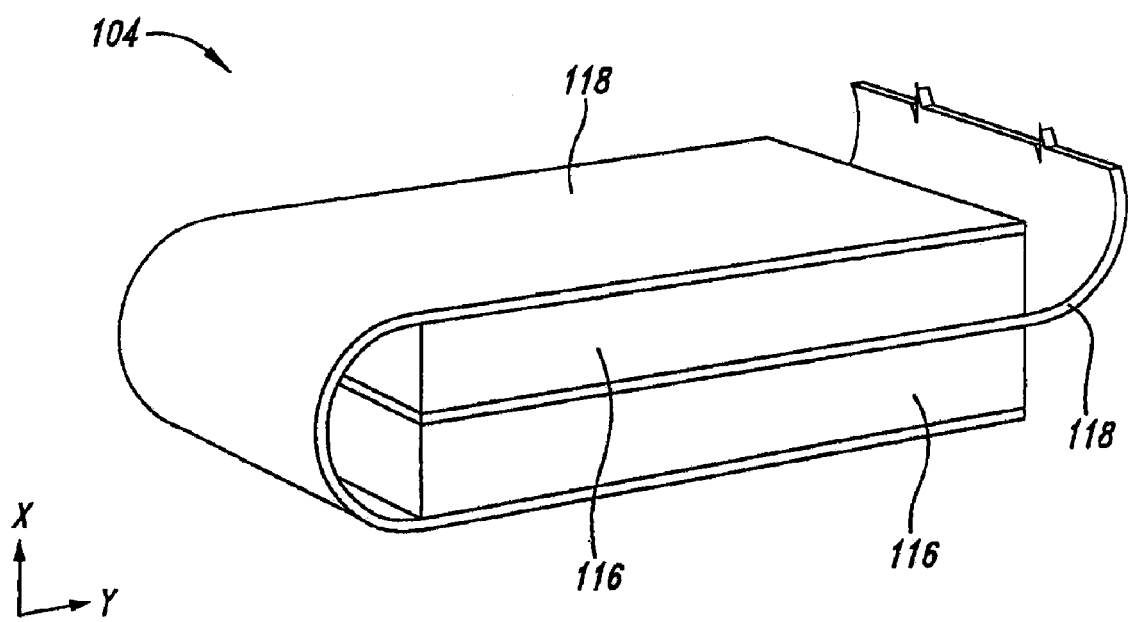
FIG. 26 is a sectional perspective view of a first high thermal conductivity (HTC) implementation of the piezoelectric element used in the thermally enhanced ultrasound transducer.

A first high thermal conductivity (HTC) implementation of the piezoelectric element 104 is shown in FIG. 26 as having piezoelectric layers 116 (such as ceramic) interleaved between high thermal conductivity (HTC) layers 118 (such as metallic electrode material). The HTC layers 118 are shown bent in a serpentine fashion to thermally couple together more than one of the HTC layers. The thermally conductive pathways of the HTC layers 118 can be oriented substantially normal to the illustrative X-dimension along the illustrative Y-dimension and parallel to the surfaces of the piezoelectric element 104 with the electrode material 104a.

Since the electrode material 104a also has a high thermal conductivity, it may also be used as remove heat from the piezoelectric element 104 using configurations discussed herein to prevent electrical shorting of the piezoelectric element. Methods to construct the first HTC implementation of the piezoelectric element 104 and other implementations include laminate construction similar to that used for multi-layer ceramic capacitors and can be used with slip-cast piezoelectric ceramic. In some implementations, a sufficient number of the piezoelectric layers 116 are used to produce enough acoustic energy for the combined ultrasound 107 with the thickness of each of the piezoelectric layers being much thinner than when the piezoelectric element is one piece.

Consequently, the first HTC implementation of the piezoelectric element 104 can have relatively short distances involved from interior locations of the piezoelectric layers 116 to thermal pathways such as provided by the HTC layers 118. The HTC layers 118 can then be thermally coupled to one or more instances of the heatsink 108 such as within housing structures of the thermally enhanced ultrasound transducer 100. When composed of electrically conductive materials, such as metal, the HTC layers 118 could also be electrically coupled together in series and/or parallel arrangements depending on the electrical properties for an HTC implementation of the piezoelectric element 104. For example, electrically conductive versions of the HTC layers 118 that are electrically coupled together in series will reduce the overall electrical capacitance of a particular HTC implementation of the piezoelectric element 104, whereas electrically conductive versions of the HTC layers that are electrically coupled together in parallel will increase the overall electrical capacitance of a particular HTC implementation of the piezoelectric element 104.

Figure 27:
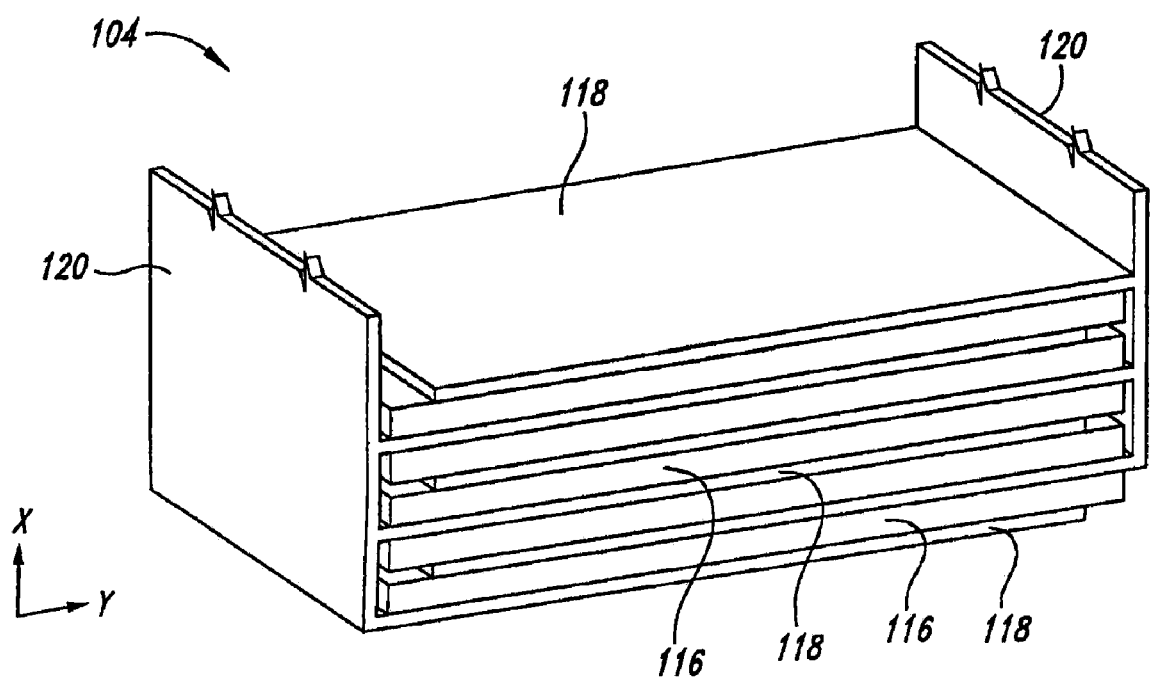
FIG. 27 is a sectional perspective view of a second HTC implementation of the piezoelectric element used in the thermally enhanced ultrasound transducer.

A second HTC implementation of the piezoelectric element 104 is shown in FIG. 27 as having multiple of the HTC layers 118 coupled to HTC side members 120 extending perpendicularly to the HTC layers. Whereas the first HTC implementation of the piezoelectric element 104 is depicted in FIG. 26 as having two of the piezoelectric layers 116, the second HTC implementation of the piezoelectric element is depicted in FIG. 27 as having five of the piezoelectric layers 116. Other HTC implementations of the piezoelectric element 104 can have various other numbers of the piezoelectric layers 116 depending upon such factors as capacity of each of the piezoelectric layers to produce ultrasound and requirement for amount of ultrasound energy to be produced.

Figure 28:
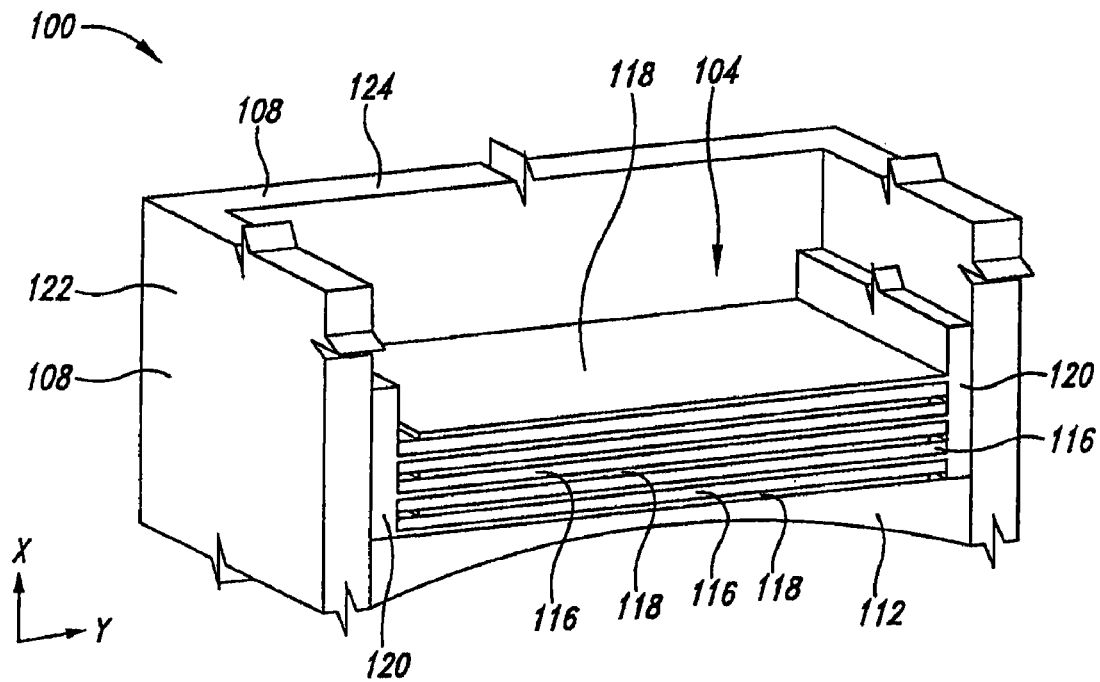
FIG. 28 is a sectional perspective view of a sixth implementation of the thermally enhanced ultrasound transducer using a third HTC implementation of the piezoelectric element of FIG. 27.

A sixth implementation of the thermally enhanced ultrasound transducer 100 is shown in FIG. 28 as using a third HTC implementation of the piezoelectric element 104 and also using a plano-concave version of the acoustic lens 112. The third HTC implementation uses laminated portions of the piezoelectric material 116 and the HTC layers 118, which can also be electrically conductive. The HTC side members 120 of the piezoelectric element 104 are positioned adjacent to side portions of a housing 122, which serve as at least one of the heat sinks 108. The HTC layers 118 also can be thermally coupled directly to back portions of the housing 124 for further removal of heat from the piezoelectric element 104.

Figure 29:
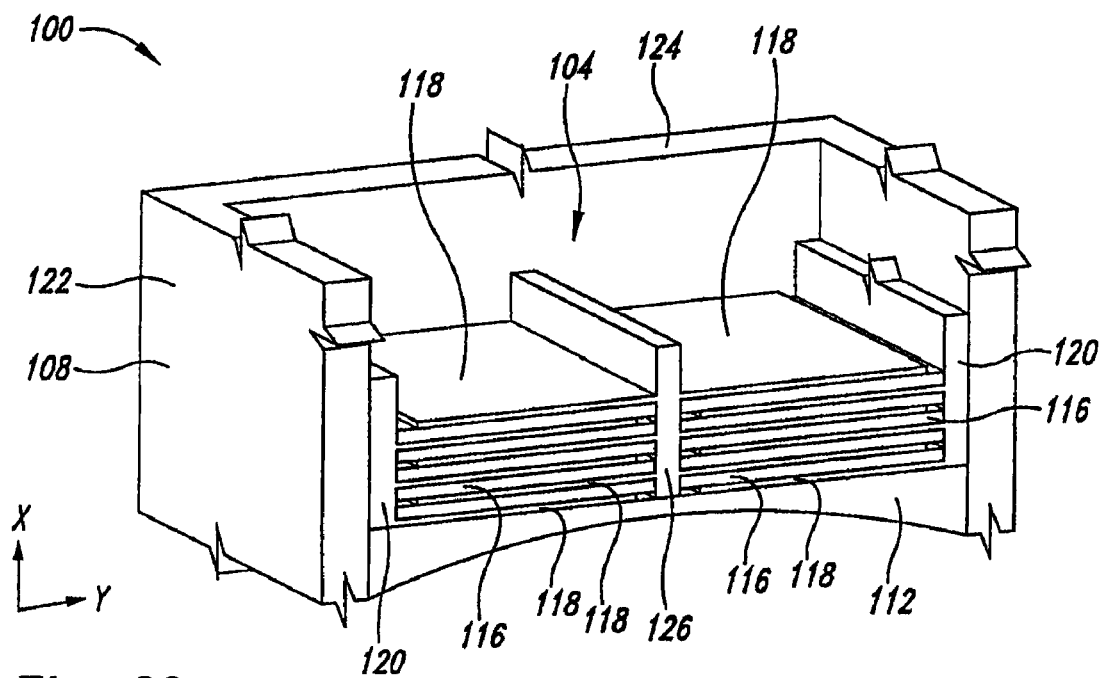
FIG. 29 is a sectional perspective view of a seventh implementation of the thermally enhanced ultrasound transducer using a fourth HTC implementation of the piezoelectric element.

A seventh implementation of the thermally enhanced ultrasound transducer 100 is shown in FIG. 29 as using a fourth HTC implementation of the piezoelectric element 104 and also using the plano-concave version of the acoustic lens 112. The fourth HTC implementation of the piezoelectric element 104 has a internally positioned HTC member 126 that effectively divides the HTC layers 118 into smaller active elements to shorten thermal pathways to remove heat from the layers of the piezoelectric material 116. Other versions of the seventh implementation of the thermally enhanced ultrasound transducer 100 can also include the rear HTC layer 102 and/or front HTC section 106 discussed above. The internally positioned HTC member 126 is coupled to the back portion of the housing 124 as one of the heat sinks 108 for further removal of heat from the piezoelectric element 104.

The third and fourth HTC implementations of the piezoelectric element 104 include versions of the HTC layers 118 that can be electrically conductive either coupled to or also serving the function of the electrode material 104a. The HTC layers 118 are thermally coupled to structural components of the thermally enhanced ultrasound transducer 100, which also act as instances of the heat sink 108. In addition, heat extraction from the piezoelectric element 104 can be further enhanced by division of the piezoelectric layers 116 and the HTC layers 118 into smaller individual components such as through the use of one or more instances of the internally positioned HTC member 126 to further shorten thermal pathways from the piezoelectric layers 118 to one or more instances of the heat sink 108.

Other implementations of the thermally enhanced ultrasound transducer 100 use the rear HTC layer 102 and/or other implementations of the front HTC section 106 to aid the removal of heat from the HTC implementations of the piezoelectric element 104.

Figure 30:
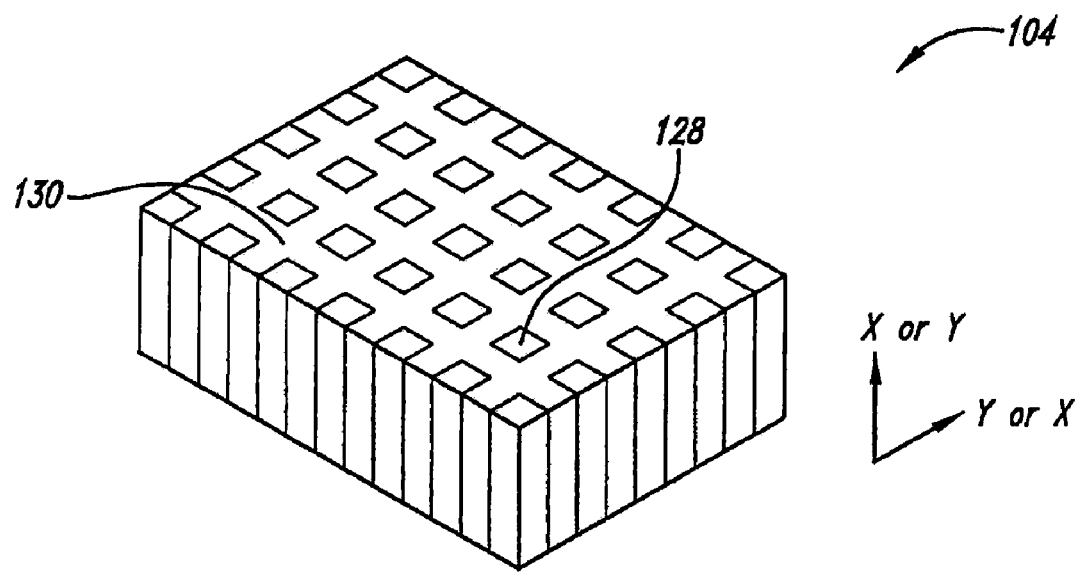
FIG. 30 is a perspective view of a first conventional composite implementation of the piezoelectric element.

A first conventional composite implementation of the piezoelectric element 14 is shown in FIG. 30 as having first piezoelectric members 128 as posts of piezoelectric ceramic. In the depicted version, the first piezoelectric members 128 extend along the illustrative X-dimension in which the combined ultrasound 107 propagates. A polymer material 130, such as epoxy, is positioned between the first piezoelectric members 128 to help remove heat away from the first piezoelectric members. The first conventional composite implementation can be formed, for instance, from a single piece of piezoelectric ceramic cut with a fine dicing saw in two orthogonal directions leaving a spaced array of the first piezoelectric members 128. The polymer material 130 is used to fill between the first piezoelectric members 128. Other dicing schemes may be applied such as dicing in one direction only or by varying spacing and dimensions of the first piezoelectric members 128.

Figure 31:
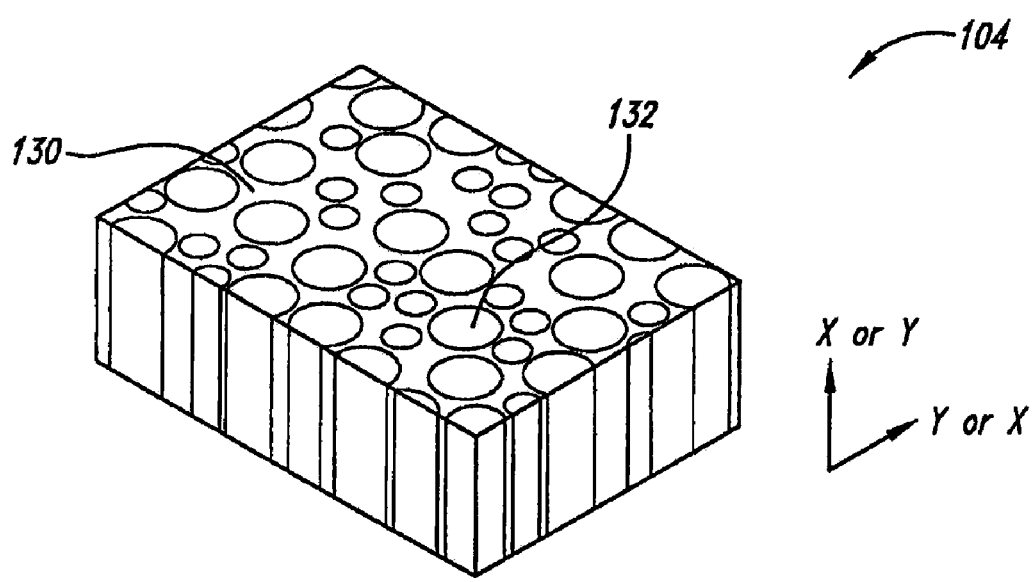
FIG. 31 is a perspective view of a second conventional composite implementation of the piezoelectric element.

A second conventional composite implementation of the piezoelectric element 14 is shown in FIG. 31 having second piezoelectric members 132 as fine piezoelectric ceramic fibers. Other spacing or sized fibers can be used in other conventional composite implementations. A conventional composite implementation of the piezoelectric element 14 can be handled in a manner similar to that for a monolithic version. Typically the first piezoelectric members 128 and the second piezoelectric members 132 account for a range of 25% to 75% (depicted as 25% in FIG. 30 and 65% in FIG. 31) of the total volume of a composite implementation of the piezoelectric element 14 for operational frequency ranges used.

Figure 32:
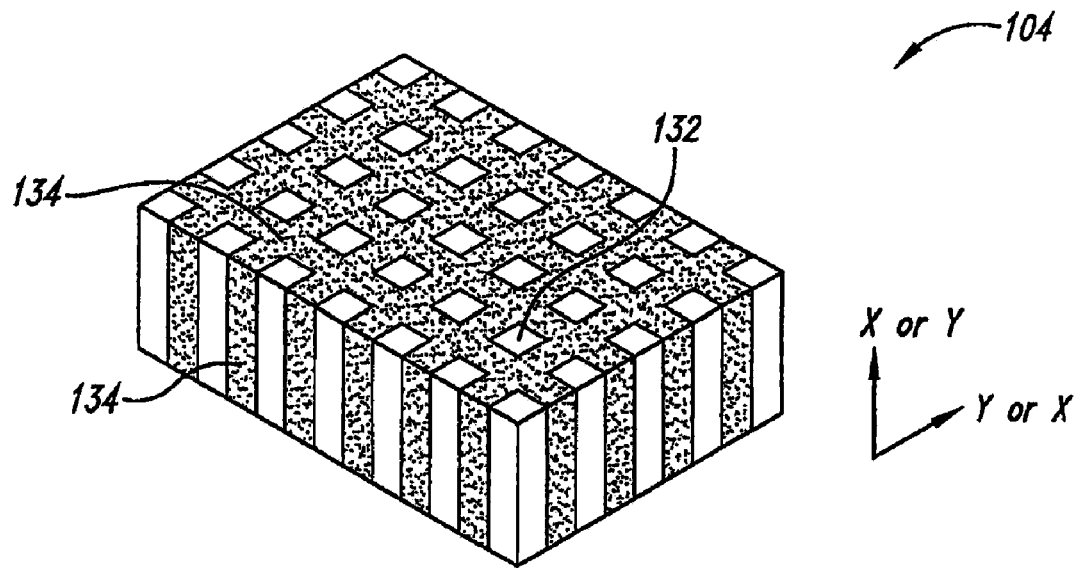
FIG. 32 is a perspective view of a fifth HTC implementation of the piezoelectric element.
Figure 33:
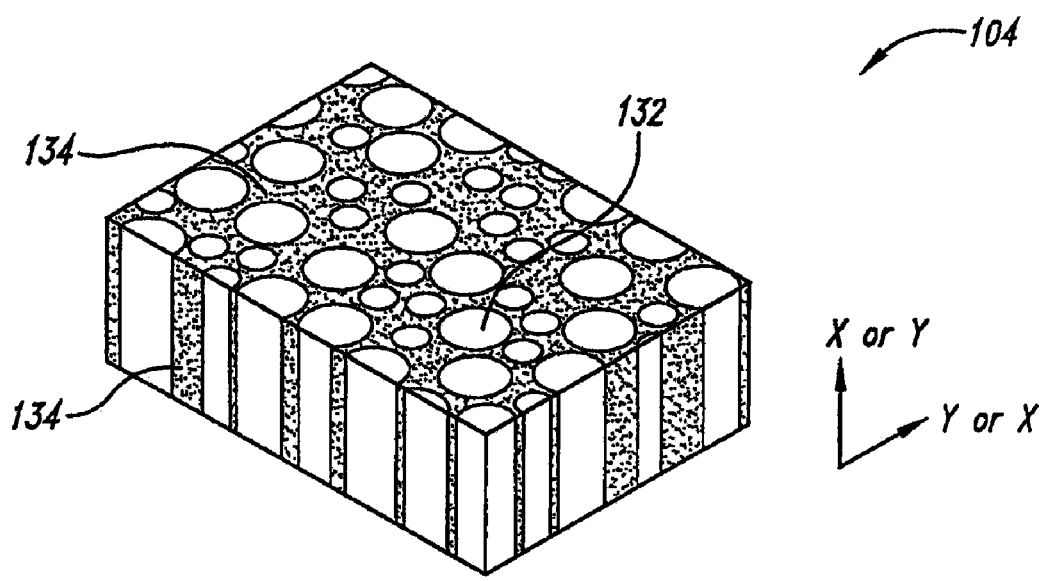
FIG. 33 is a perspective view of a sixth HTC implementation of the piezoelectric element.

A fifth HTC implementation of the piezoelectric element 104 is shown in FIG. 32 as having the first piezoelectric members 128 positioned between an aggregate HTC thermally conductive material 134. A sixth HTC implementation of the piezoelectric element 104 is shown in FIG. 33 as having the second piezoelectric members 132 positioned between the aggregate HTC material 134. Versions of the aggregate HTC material 134 include the polymer material 130 mixed with particles that have high thermal conductivity and are electrically insulating, such as from materials including, but not limited to aluminum oxide, aluminum nitride, zinc oxide, sapphire, and diamond. Because of the relatively close packing of the first piezoelectric members 128 and/or the second piezoelectric members 132, such as on the order of a few microns, heat flow readily occurs to the aggregate HTC material 134 on to other heat dissipating structures such as one or more instances of the heat sink 108.

In alternative implementations, high thermal materials 136 are incorporated directly with piezoelectric material 138, as shown in FIG. 34, to form monolithic HTC versions of the piezoelectric element 104, and the piezoelectric material 116, the first piezoelectric members 128, and/or the second piezoelectric members 132. The high thermal materials 136 as thermally conductive, electrically insulating powder can be incorporated by custom blending with the piezoelectric material 138 as piezoelectric ceramic powder prior to firing.

The high thermal materials 136 include, but not limited to, aluminum oxide, aluminum nitride, zinc oxide, sapphire, and diamond. Particle size of the high thermal materials 136 can be in the range of 20 to 200 microns which are large relative to the particles of the piezoelectric material 138 (which typically are a few microns or less in diameter) and smaller than the thickness of a typical version of the piezoelectric element 104, and the piezoelectric material 116, the first piezoelectric members 128, and/or the second piezoelectric members 132. Relatively large particle sizes for the high thermal materials 136 are chosen so that the interfaces between the fine grain particles of the piezoelectric material 138 remain and piezoelectric performance is maintained. Large particle sizes for the high thermal materials 136 have the further advantage of increased heat transfer.

From the foregoing it will be appreciated that, although specific embodiments of the invention have been described herein for purposes of illustration, various modifications may be made without deviating from the spirit and scope of the invention. For instance, for reasons including ease of illustration, rectangular and plano-concave shapes were used for depicted implementations; however, other implementations can use other shapes while staying with the spirit and scope of the invention. Accordingly, the invention is not limited by only those implementations described in detail herein.

The invention claimed is:

1. For a high intensity focused ultrasound (HIFU) transducer configured to transmit ultrasound having at least a first frequency of at least 100 KHz along a first dimension toward a front medium, a piezoelectric element comprising:

a plurality of piezoelectric layers including a first piezoelectric layer and a second piezoelectric layer, each piezoelectric layer configured to produce the ultrasound;

a plurality of high thermal conductivity (HTC) layers including a first HTC layer, a second HTC layer, and a third HTC layer, each HTC layer having a thermal conductivity of at least 100 W/mC, the first piezoelectric layer in juxtaposition between the first HTC layer and the second HTC layer along the first dimension, the second piezoelectric layer in juxtaposition between the second HTC layer and the third HTC layer along the first dimension;

a first HTC side member having a thermal conductivity of at least 100 W/mC, the first HTC side member extending along the first dimension; and a second HTC side member having a thermal conductivity of at least 100 W/mC, the first HTC side member extending along the first dimension, the plurality of HTC layers thermally coupled to and extending between the first HTC side member and the second HTC side member, and the plurality of piezoelectric layers coupled to and extending between the first HTC side member and the second HTC side member; and a housing including a first side portion and a second side portion, wherein the first HTC side member is thermally coupled to the first side portion of the housing and the second HTC side member is thermally coupled to the second side portion of the housing.

2. The piezoelectric element of claim 1 wherein the plurality of HTC layers have a thermal conductivity equal to the thermal conductivity of one of the following materials: gold, pure synthetic diamond, silver, bronze, or aluminum.

3. For a high intensity focused ultrasound (HIFU) transducer configured to transmit ultrasound having at least a first frequency of greater than 100 KHz and less than 10 MHz, a piezoelectric element comprising:

a plurality of high thermal conductivity (HTC) layers, each HTC layer having a thermal conductivity of at least 100 W/mC, each HTC layer including a first parallel portion and a second parallel portion positioned substantially parallel to one another and including a third portion extending from the first parallel portion to the second parallel portion wherein the plurality of HTC layers have a thermal conductivity equal to the thermal conductivity of pure synthetic diamond; and a plurality of piezoelectric layers, each of the piezoelectric layers configured to produce the ultrasound, each of the piezoelectric layers being positioned between the first parallel portion and the second parallel portion of a different one of the HTC layers (HTC) layers.

4. For a high intensity focused ultrasound (HIFU) transducer configured to transmit ultrasound having at least a first frequency of greater than 100KHz and less than 10 MHz, a piezoelectric element comprising:

a plurality of high thermal conductivity (HTC) layers, each HTC layer having a thermal conductivity of at least 100 W/mC, each HTC layer including a first parallel portion and a second parallel portion positioned substantially parallel to one another and including a third portion extending from the first parallel portion to the second parallel portion;

a plurality of piezoelectric layers, each of the piezoelectric layers configured to produce the ultrasound, each of the piezoelectric layers being positioned between the first parallel portion and the second parallel portion of a different one of the HTC layers (HTC) layers; and a housing containing the HIFU transducer, the housing being thermally coupled with the third portions of each of the plurality of HTC layers.

5. The piezoelectric element of claim 4 wherein the plurality of HTC layers have a thermal conductivity equal to the thermal conductivity of gold, pure synthetic diamond, silver, bronze, and aluminum.

6. The piezoelectric element of claim 4 wherein the plurality of HTC layers have a thermal conductivity equal to the thermal conductivity of pure synthetic diamond.

7. The piezoelectric element of claim 4 wherein the plurality of HTC layers have a thermal conductivity equal to the thermal conductivity of silver.

8. The piezoelectric element of claim 4 wherein the plurality of HTC layers have a thermal conductivity equal to the thermal conductivity of bronze.

9. The piezoelectric element of claim 4 wherein the plurality of HTC layers have a thermal conductivity equal to the thermal conductivity of aluminum.

* * * * *